United States Patent
Cressina et al.

(10) Patent No.: US 10,526,648 B2
(45) Date of Patent: Jan. 7, 2020

(54) SHORT PENDANT ARM LINKERS FOR NUCLEOTIDES IN SEQUENCING APPLICATIONS

(71) Applicant: ILLUMINA CAMBRIDGE LIMITED, Nr. Saffron Walden (GB)

(72) Inventors: Elena Cressina, Nr. Saffron Walden (GB); Antoine Francais, Nr. Saffron Walden (GB); Xiaohai Liu, Nr. Saffron Walden (GB)

(73) Assignee: Illumina Cambridge Limited, Cambridge (GB)

(*) Notice: Subject to any disclaimer, the term of this patent is extended or adjusted under 35 U.S.C. 154(b) by 0 days.

(21) Appl. No.: 16/033,118

(22) Filed: Jul. 11, 2018

(65) Prior Publication Data

US 2019/0017111 A1   Jan. 17, 2019

(30) Foreign Application Priority Data

Jul. 12, 2017 (GB) .................................. 1711219.4

(51) Int. Cl.

| | |
|---|---|
| *C12Q 1/68* | (2018.01) |
| *C07H 19/10* | (2006.01) |
| *C12Q 1/6869* | (2018.01) |
| *C07H 19/073* | (2006.01) |
| *C07H 19/14* | (2006.01) |
| *C07H 21/04* | (2006.01) |
| *C12Q 1/6809* | (2018.01) |
| *C12Q 1/6816* | (2018.01) |

(52) U.S. Cl.
CPC ......... *C12Q 1/6869* (2013.01); *C07H 19/073* (2013.01); *C07H 19/14* (2013.01); *C07H 21/04* (2013.01); *C12Q 1/6809* (2013.01); *C12Q 1/6816* (2013.01)

(58) Field of Classification Search
CPC .............................. C12Q 1/6869; C07H 19/10
USPC .................................. 536/4.1, 23.1; 435/6.1
See application file for complete search history.

(56) References Cited

U.S. PATENT DOCUMENTS

| | | | |
|---|---|---|---|
| 5,268,486 A | 12/1993 | Waggoner et al. | |
| 5,302,509 A | 4/1994 | Cheeseman | |
| 6,465,178 B2 | 10/2002 | Chappa et al. | |
| 6,924,372 B2 | 8/2005 | Czerney et al. | |

FOREIGN PATENT DOCUMENTS

| | | |
|---|---|---|
| WO | WO 1998/044151 | 10/1998 |
| WO | WO 2000/006770 | 7/1999 |
| WO | WO 2000/018957 | 4/2000 |
| WO | WO 2000/031148 | 6/2000 |
| WO | WO 2000/053812 | 9/2000 |
| WO | WO 2001/001143 | 1/2001 |
| WO | WO 2001/057248 | 8/2001 |
| WO | WO 2002/012566 | 2/2002 |
| WO | WO 2002/026891 | 4/2002 |
| WO | WO 2003/014392 | 2/2003 |
| WO | WO 2004/018497 | 3/2004 |
| WO | WO 2005/024010 | 3/2005 |
| WO | WO 2005/047301 | 5/2005 |
| WO | WO 2005/065814 | 7/2005 |
| WO | WO 2006/120433 | 11/2006 |
| WO | WO 07/020457 | 2/2007 |
| WO | WO 14/135223 | 9/2014 |

OTHER PUBLICATIONS

Margulies et al., "Genome sequencing in microfabricated high-density picolitre reactors", Nature. 437, 376-380 (2005).
Shendure et al., "Accurate multiplex polony sequencing of an evolved bacterial genome", Science. 309, 5741, 1728-1732 (2005).
Scheit, Nucleotide analogs (John Wiley & Son, 1980), Table of Content.
Uhlmann et al., "Antisense oligonucleotides: a new therapeutic principle", Chemical Reviews 90:543-584, 1990.
International Search Report and Written Opinion dated Oct. 9, 2018 in International Application No. PCT/EP2018/069030.

*Primary Examiner* — Jezia Riley
(74) *Attorney, Agent, or Firm* — Knobbe, Martens, Olson & Bear, LLP

(57) ABSTRACT

The present disclosure relates to new nucleotide and oligonucleotide compounds and their use in nucleic acid sequencing applications.

23 Claims, 5 Drawing Sheets

FIG. 4A
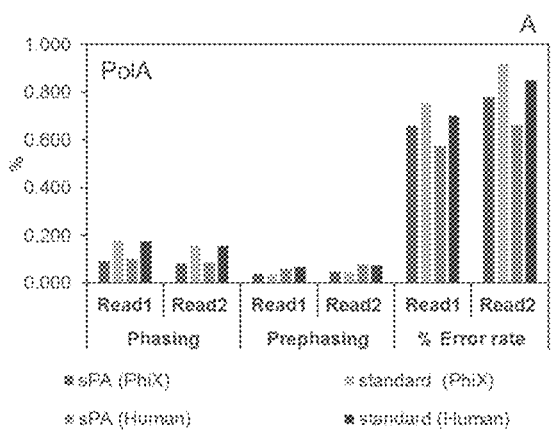
FIG. 4B
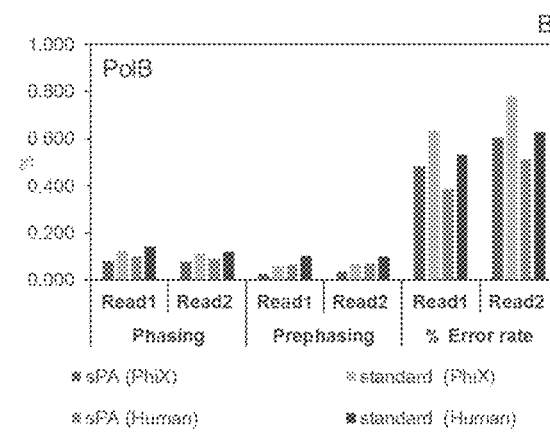
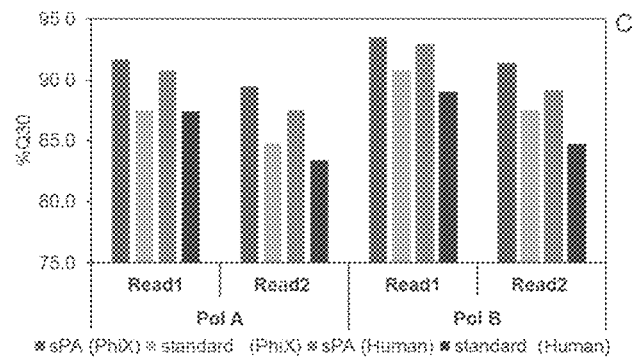
FIG. 4C

FIG. 5A
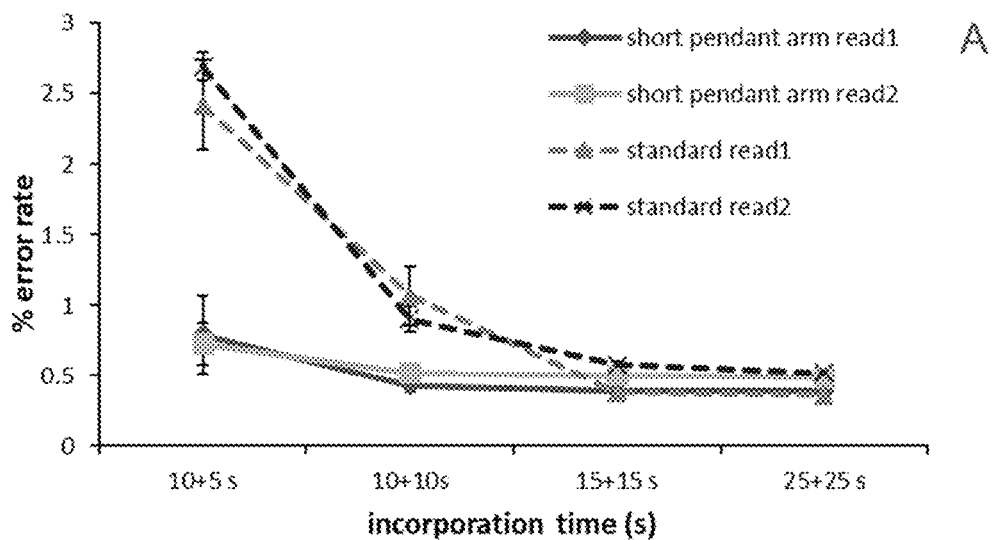
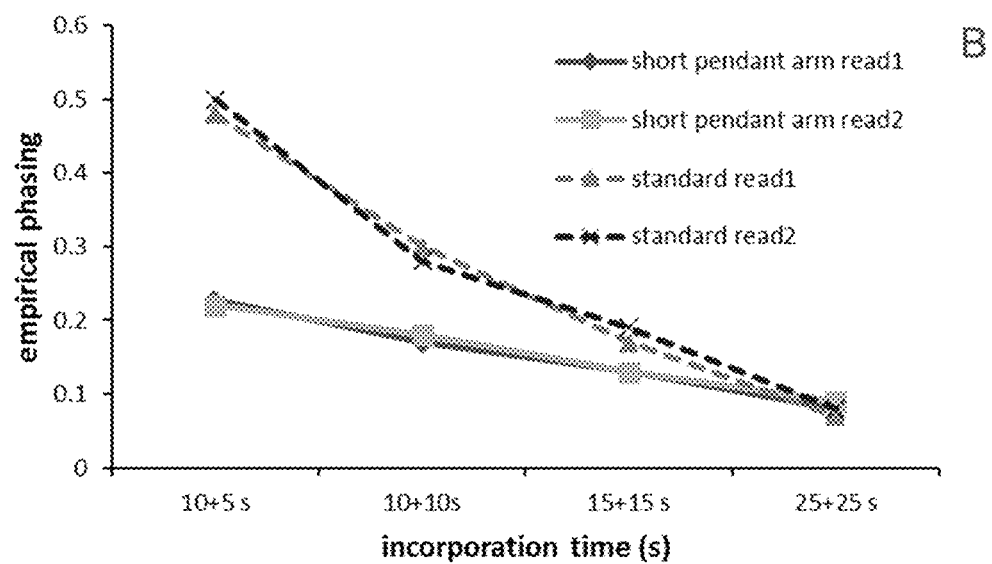
FIG. 5B

SHORT PENDANT ARM LINKERS FOR NUCLEOTIDES IN SEQUENCING APPLICATIONS

INCORPORATION BY REFERENCE TO ANY PRIORITY APPLICATIONS

The present application claims the benefit of priority to United Kingdom (GB) Application No. 1711219.4, filed Jul. 12, 2017, which is incorporated by reference in its entirety.

BACKGROUND

Field

The present disclosure relates to new nucleotide and oligonucleotide compounds and their use in nucleic acid sequencing applications.

Description of the Related Art

As sequencing technology advances a need has developed for improved sequencing reagents which are amenable particularly to high throughput molecular methods such as solid phase sequencing and the like.

In certain types of high-throughput sequencing, the nucleotides used contain fluorophores which specifically identify the incorporated base. The fluorophore can be attached to the nucleotide base through a cleavable linker. Therefore after the incorporated base is identified, the linker can be cleaved, allowing the fluorophore to be removed ready for the next base to be attached and identified. Such a cleavage leaves a remaining "scar" or "pendant arm" moiety located on each of the detected nucleobases. Whilst it is possible to design reagents that do not leave any trace following cleavage, these tend to be slow to cleave and hence are not particularly efficacious. A balance needs to be found between efficient incorporation of the labeled nucleotides, efficient cleavage to remove all the incorporated labels, and efficient incorporation of the following nucleotide. Described herein in are optimized nucleotide structures that improve the performance of prior art nucleotides in Sequencing-by-Synthesis (SBS) cycles.

Suitable nucleotide linkers are described in for example WO2004/018493. Compounds disclosed therein are shown as example formula (e):

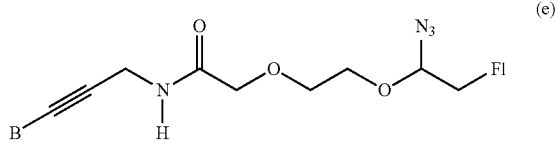

(e)

wherein B is a nucleoside base; and Fl is a fluorophore attached through an optional linker. This is cleaved to leave a pendant arm moiety of formula (ei):

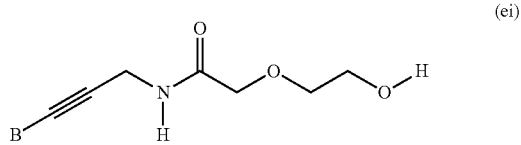

(ei)

Applicants have realized that alterations to the pendant arm can give improvements to the sequencing data obtained.

Described herein are improved nucleotide structures and their use in sequencing. The molecules described can be incorporated into nucleic acid strands. Described also are nucleic acid strands having certain modifications which allow for more efficient nucleotide incorporation. Also described are nucleic acid arrays and the use thereof in sequencing. Particular improvements can be seen in the efficiency of labelled nucleotide incorporation and length and accuracy of sequencing read obtainable using the new constructs. The molecules described below are particularly advantageous in situations where long read lengths are required, or where shorter nucleotide incorporation times are advantageous. high power excitation sources are used.

SUMMARY

The present disclosure relates to improved reagents for nucleic acid sequencing. During repeated cycles of sequencing-by-synthesis (SBS) where fluorescently labelled nucleotides are incorporated into an extended nucleic acid strand, a "scarred" DNA primer:template is produced. The "scar" or "pendant arm", is a moiety located on each of the detected nucleobases, resulting from the chemical cleavage of the fluorophore from the nucleobase to which it is attached. These pendant arms accumulate on the DNA primer:template over the repeated SBS cycles, producing a primer:template DNA molecule with molecular structure that differs from a natural DNA primer:template. These residual pendant arms slow down the incorporation of the new incoming nucleotide and, therefore increase the error rate, and lower the data quality, especially at the later stages of a sequencing run and over long sequencing runs. FIG. 1 exemplifies the formation of a scarred or pendant arm DNA primer:template during sequencing. The present disclosure aims at minimizing the size of pendant arm left on DNA primer:template during sequencing.

According to a first aspect this disclosure provides compounds of the formula (I):

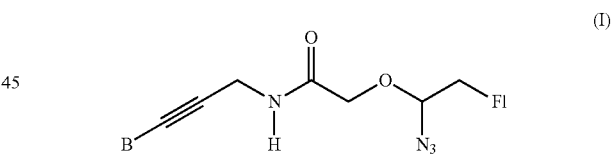

(I)

wherein B is a nucleoside base; and Fl is a fluorophore attached through an optional linker.

Nucleosides are compounds having a carbohydrate ribose attached to a nucleobase. The nucleobase can be a purine or a pyrimidine. The common naturally occurring purines are adenine (A) and guanine (G). The common naturally occurring pyrimidines are cytidine (C) and thymine (T) in DNA strands or uracil (U) in RNA strands. The ribose can be a 2'-deoxyribose (in DNA). A nucleoside having a phosphate moiety attached thereto is a nucleotide, and thus the compounds described herein can be in the form of a nucleotide. In any formulas described herein, B can represent a nucleotide base.

In any formulas described herein, B can represent a pyrimidine base. The base B can take the form of any of the four common naturally occurring bases, A, G, C or T/U. The phosphate moiety can be a triphosphate moiety, which can be attached to the 5'-position of the ribose. Compounds of the present disclosure can include compounds of the following formula (c), formula (t) or formula (a):

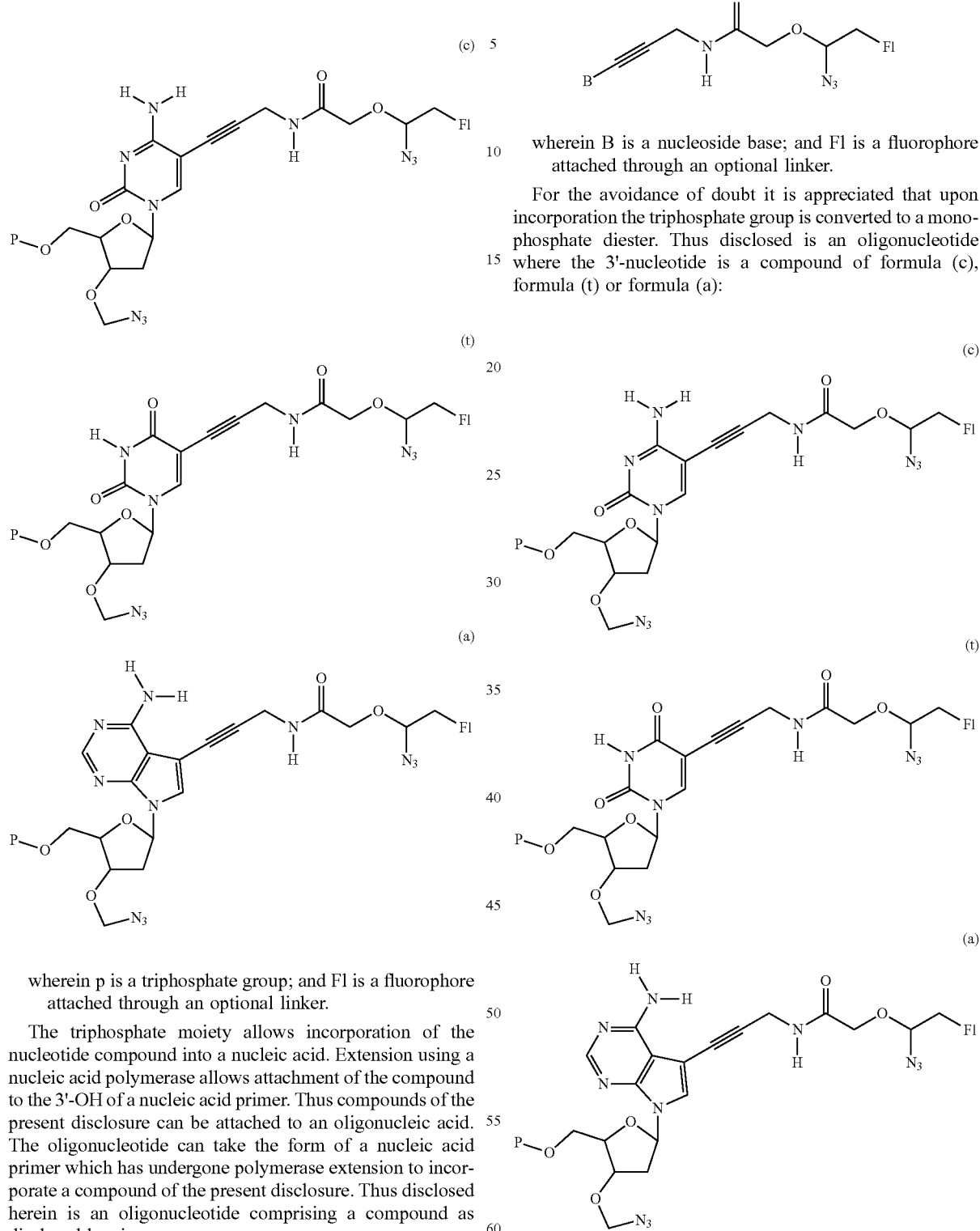

wherein p is a triphosphate group; and Fl is a fluorophore attached through an optional linker.

The triphosphate moiety allows incorporation of the nucleotide compound into a nucleic acid. Extension using a nucleic acid polymerase allows attachment of the compound to the 3'-OH of a nucleic acid primer. Thus compounds of the present disclosure can be attached to an oligonucleic acid. The oligonucleotide can take the form of a nucleic acid primer which has undergone polymerase extension to incorporate a compound of the present disclosure. Thus disclosed herein is an oligonucleotide comprising a compound as disclosed herein.

Disclosed is a nucleotide compounds attached to an oligonucleotide. Where the compound is fluorescently labelled, generally only a single modified compound would be attached to each oligonucleotide. Thus disclosed is an oligonucleotide where the 3'-nucleotide is a compound of formula (I):

wherein B is a nucleoside base; and Fl is a fluorophore attached through an optional linker.

For the avoidance of doubt it is appreciated that upon incorporation the triphosphate group is converted to a monophosphate diester. Thus disclosed is an oligonucleotide where the 3'-nucleotide is a compound of formula (c), formula (t) or formula (a):

wherein p is a monophosphate group; and Fl is a fluorophore attached through an optional linker.

Compounds above can alternately be represented as an oligonucleotide where the 3'-nucleotide is a compound of formula (c), formula (t) or formula (a):

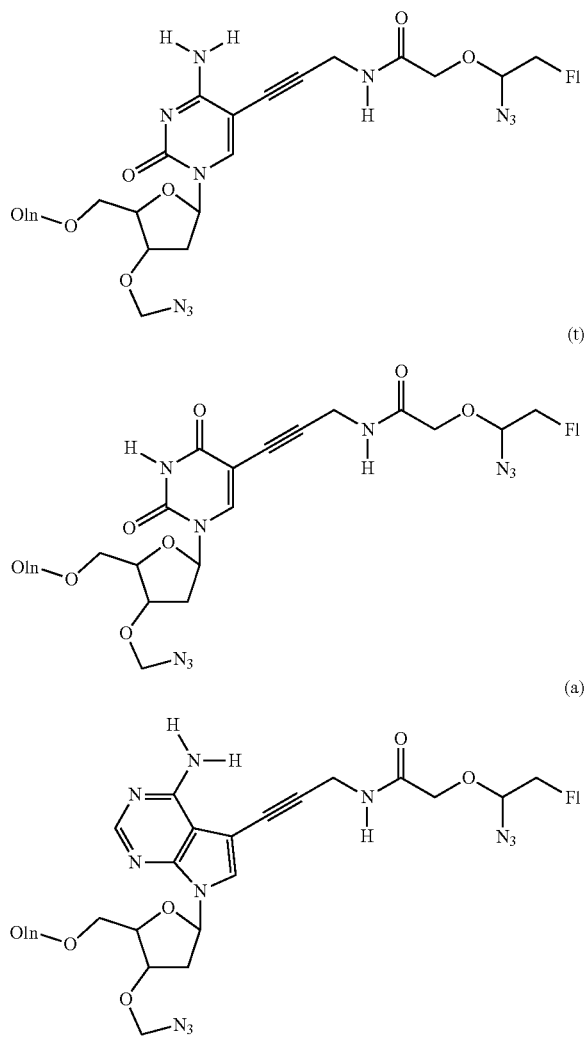

wherein Oln is an oligonucleotide; and Fl is a fluorophore attached through an optional linker.

Upon detection of the nucleobase incorporated, the fluorescent label and optional linker can be removed. The removal is carried out by reduction of the azido group, leading to fragmentation of the O—CHNH$_2$— moiety. Upon cleavage a hydroxyl group is left attached to the nucleobase and the fluorescent moiety is detached.

Thus disclosed is a compound of the formula (II):

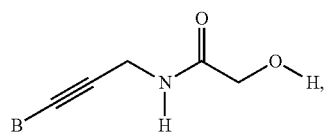

(II)

wherein B is a nucleotide base.

The nucleobase can be a purine or a pyrimidine. The common naturally occurring purines are adenine (A) and guanine (G). The common naturally occurring pyrimidines are cytidine (C) and thymine (T) in DNA strands or uracil (U) in RNA strands. The ribose can be a 2'-deoxyribose (in DNA).

The compound of formula II can be attached to an oligonucleotide. Thus moiety B can be a base attached to further bases. Thus disclosed is an oligonucleotide where the 3'-nucleotide is a compound of formula (ci), formula (ti) or formula (ai):

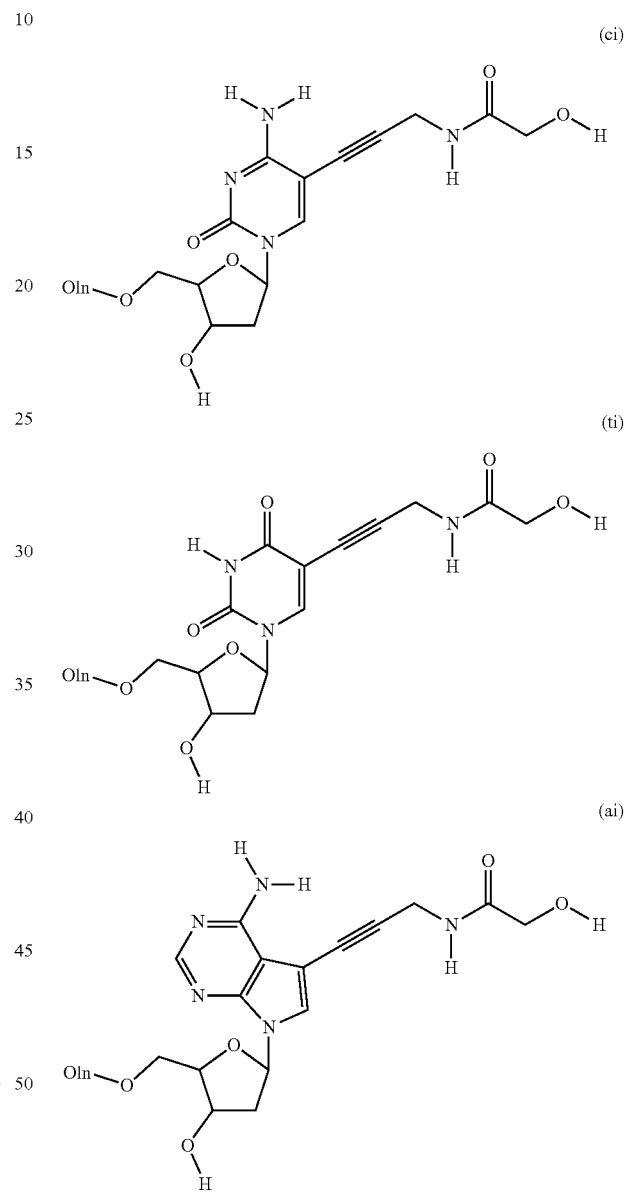

wherein Oln is an oligonucleotide.

The oligonucleotide having the hydroxyl pendant arm can have multiple pendant arms on the same oligonucleotide. The bases modified with the pendant arms would usually be contiguous in a sequence. Disclosed is an oligonucleotide comprising two or more copies of a compound according to formula (II). Disclosed is an oligonucleotide comprising ten or more copies of a compound according to formula (II). Disclosed is an oligonucleotide comprising one hundred or more copies of a compound according to formula (II).

Incorporation of nucleotides can be performed using solutions having more than one type of nucleotide. Thus disclosed is a kit comprising two or more nucleotides wherein at least one nucleotide is a labelled nucleotide as described herein. The kit may comprise two or more nucleotides wherein at least two nucleotides are labelled nucleotides as described herein. The kit may comprise four nucleotides wherein at least two nucleotides are labelled nucleotides as described herein.

The nucleosides, nucleotides, oligonucleotides and kits as described herein can be used in sequencing, expression analysis, hybridization analysis, genetic analysis, RNA analysis, or protein binding assays, or combinations thereof.

BRIEF DESCRIPTION OF THE DRAWINGS

FIGS. 4A-4C demonstrate an example of the sequencing metrics observed with the standard and the short-pendant arm nucleotides on a 2-channel modified Hiseq® with two different polymerases (PolA and PolB) and two different template libraries (PhiX and human).

FIGS. 5A and 5B demonstrate an example of the sequencing metrics observed with either the standard or the short-pendant arm nucleotides on a 2-channel modified Miseq®.

DETAILED DESCRIPTION

Figure 1:
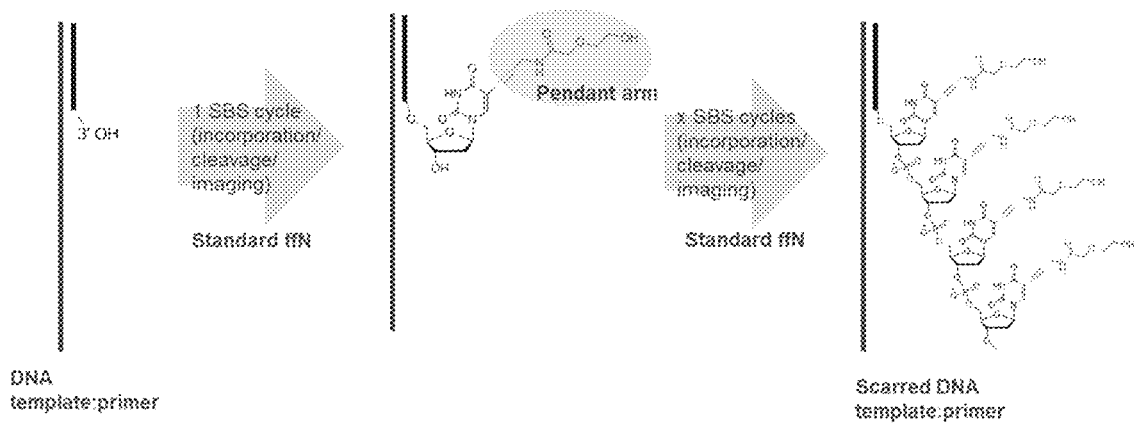
FIG. 1 illustrates the formation of scarred or pendant arm DNA primer:template during sequencing.
Figure 2:
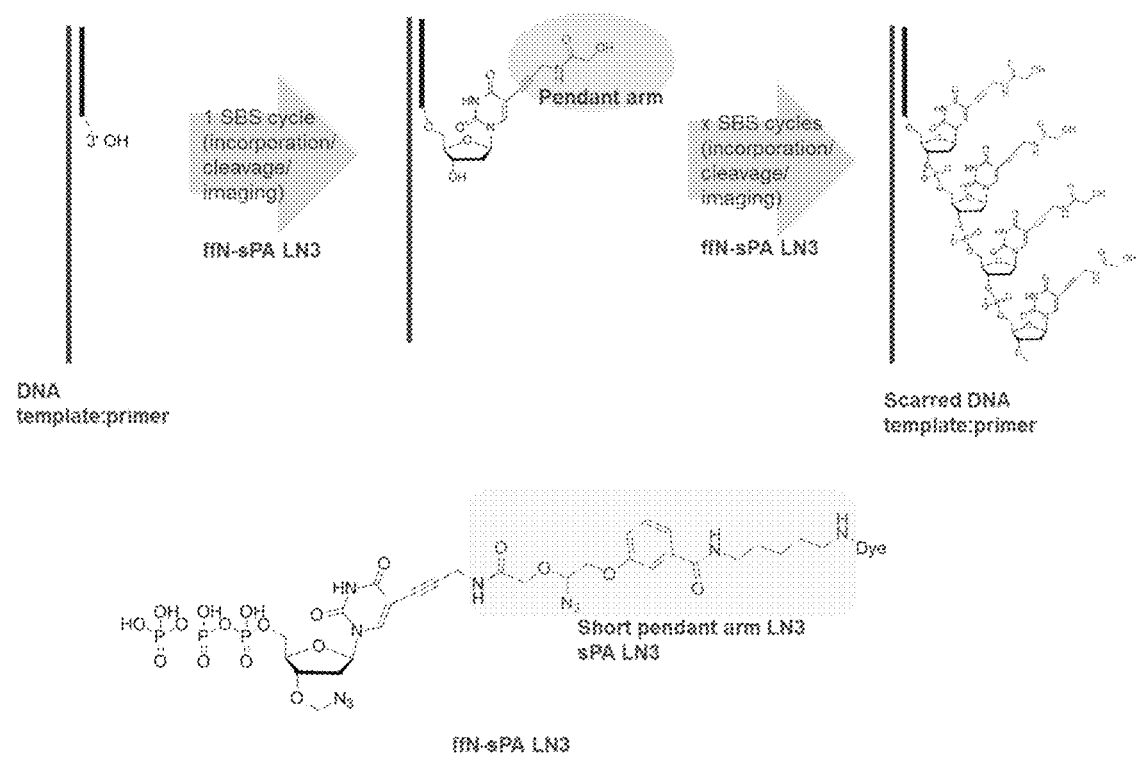
FIG. 2 illustrates an example of the structure of short pendant arm fully functionalized nucleotide (ffN) used during sequencing.

This disclosure provides novel compounds particularly suitable for methods of fluorescence detection and sequencing by synthesis. Compounds having a shortened residual pendant arm improve certain nucleic acid sequencing applications.

According to a first aspect this disclosure provides compounds of the formula (I)

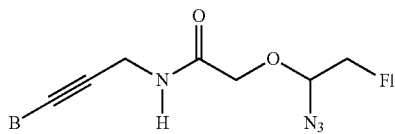

(I)

wherein B is a nucleoside base; and Fl is a fluorophore attached through an optional linker.

Nucleosides are compounds have a carbohydrate ribose attached to a nucleobase. The nucleobase can be a purine or a pyrimidine. The common naturally occurring purines are adenine (A) and guanine (G). The common naturally occurring pyrimidines are cytidine (C) and thymine (T) in DNA strands or uracil (U) in RNA strands. The ribose can be a 2'-deoxyribose (in DNA). A nucleoside having a phosphate moiety attached thereto is a nucleotide, and thus the compounds described herein can be in the form of a nucleotide. In any formulas described herein, B can represent a nucleotide base.

Fl is a fluorophore. Thus the compounds of the present disclosure are fluorescently labelled. The nature of the fluorophore is not important and can include compounds selected from any known fluorescent species, for example rhodamines or cyanines. The fluorophore can be attached to the nucleobase via an optional linker. The function of the linker is generally to aid chemical attachment of the fluorophore to the nucleotide. The linker can be for example an alkyl chain optionally having one or more heteroatom replacements. The linker may contain amide or ester groups in order to facilitate chemical coupling reactions. The linker may be synthesized using click chemistry. The linker may contain triazole groups. The linker may contain other aryl groups.

Examples of linkers may include species such as the following:

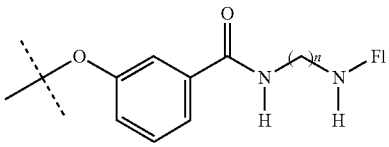

where n is an integer from 2 to 6 and Fl is a fluorophore.

The ribose moiety of the nucleoside or nucleotide may be a ribose or deoxyribose. The ribose may have one or more 2' or 3' blocking groups in order to limit incorporation to a single nucleotide. The blocking group may be an azidomethyl group. The ribose may be a 2'-deoxyribose having a 3'-azidomethyl blocking group. The blocking group may be an allyl group. The ribose may be a 2'-deoxyribose having a 3'-allyl blocking group.

In any formulas described herein, B can represent a pyrimidine base. The base B can take the form of any of the four common naturally occurring bases, A, G, C or T/U. The phosphate moiety can be a triphosphate moiety, which can be attached to the 5'-position of the ribose. Compounds of the present disclosure can include compounds of the following formula (cl), formula (tl) or formula (al):

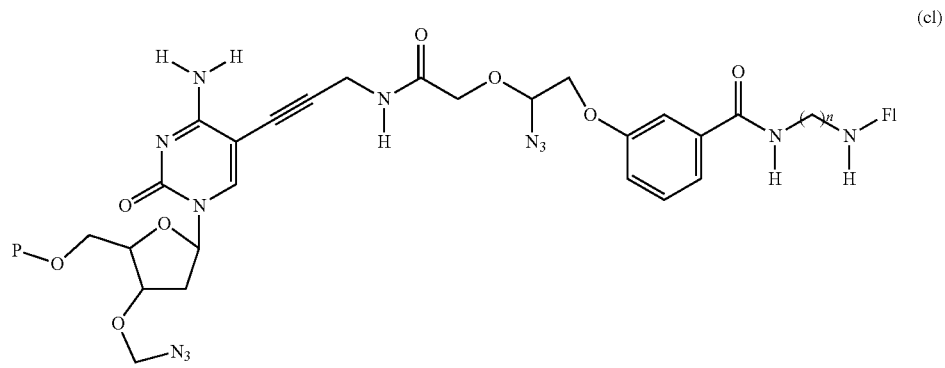

(cl)

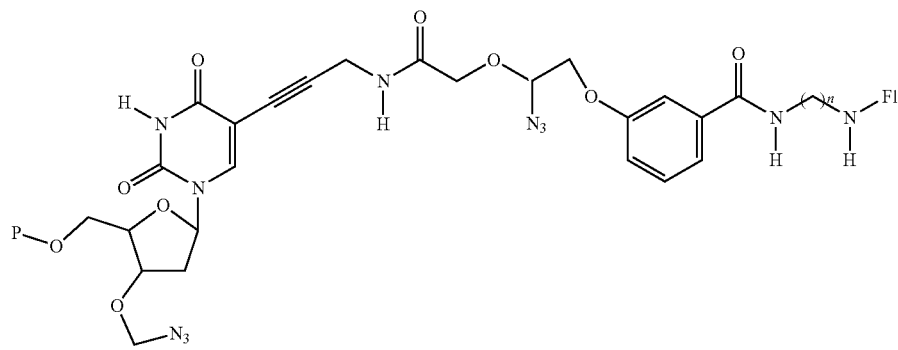

(tl)

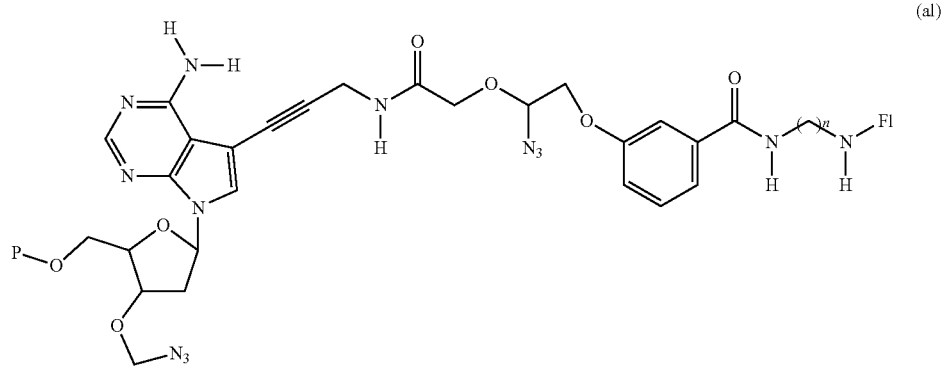

(al)

wherein p is a triphosphate group; n is an integer from 2 to 6; and Fl is a fluorophore.

The triphosphate moiety allows incorporation of the nucleotide compound into a nucleic acid. Extension using a nucleic acid polymerase allows attachment of the compound to the 3'-OH of a nucleic acid primer. Thus compounds of the present disclosure can be attached to an oligonucleic acid. The oligonucleotide can take the form of a nucleic acid primer which has undergone polymerase extension to incorporate a compound of the present disclosure. Thus disclosed herein is an oligonucleotide comprising a compound as disclosed herein.

Disclosed is a nucleotide compounds attached to an oligonucleotide. Where the compound is fluorescently labelled, generally only a single modified compound would be attached to each oligonucleotide. Thus disclosed is an oligonucleotide where the 3'-nucleotide is a compound of formula (III):

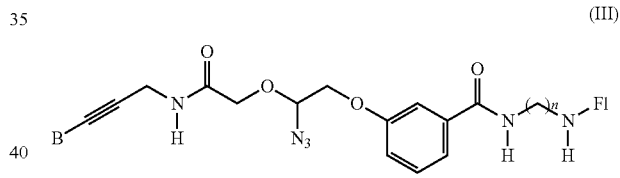

(III)

wherein B is a nucleoside base; n is an integer from 2 to 6; and Fl is a fluorophore.

For the avoidance of doubt it is appreciated that upon incorporation the triphosphate group is converted to a monophosphate di-ester. Thus disclosed is an oligonucleotide where the 3'-nucleotide is a compound of formula (cl), formula (tl) or formula (al):

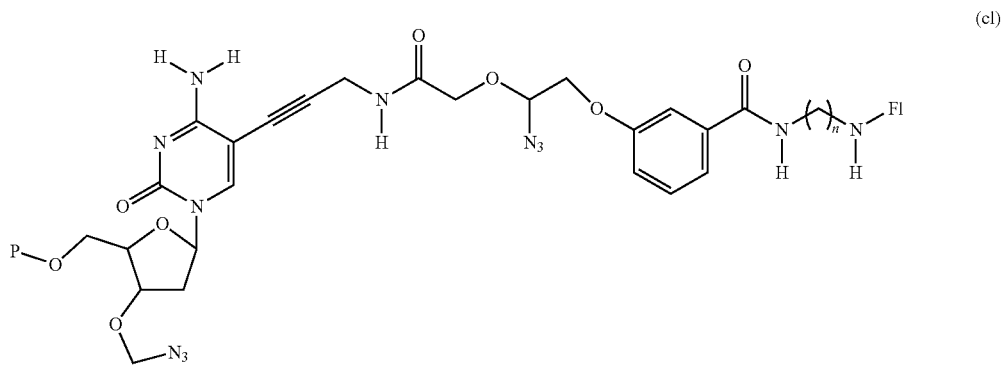

(cl)

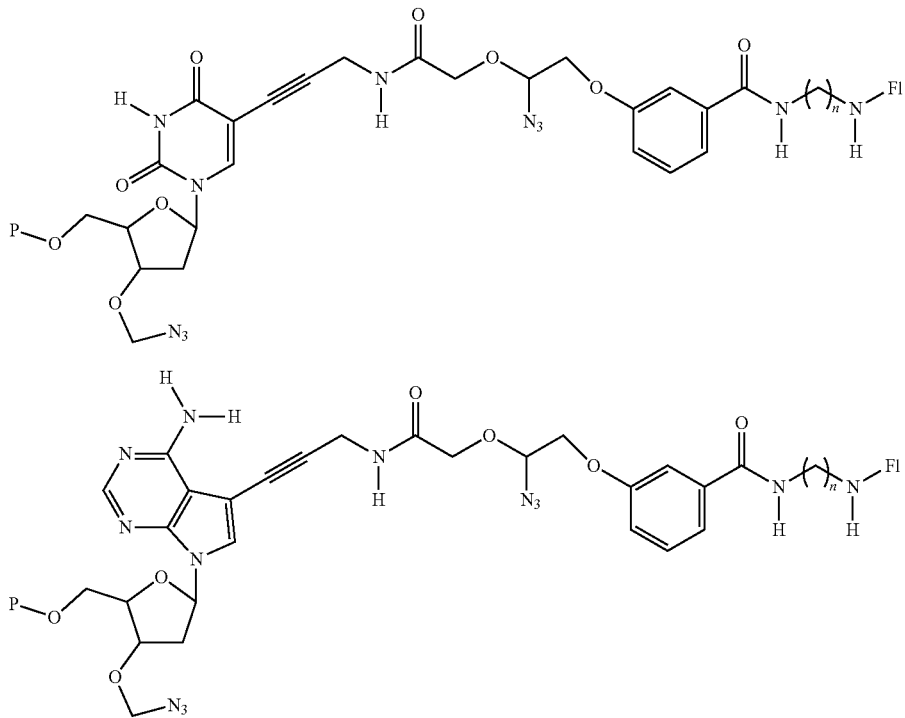
wherein p is a monophosphate group; n is an integer from 2 to 6; and Fl is a fluorophore.
Compounds above can alternately be represented as an oligonucleotide where the 3'-nucleotide is a compound of formula (cl), formula (tl) or formula (al):
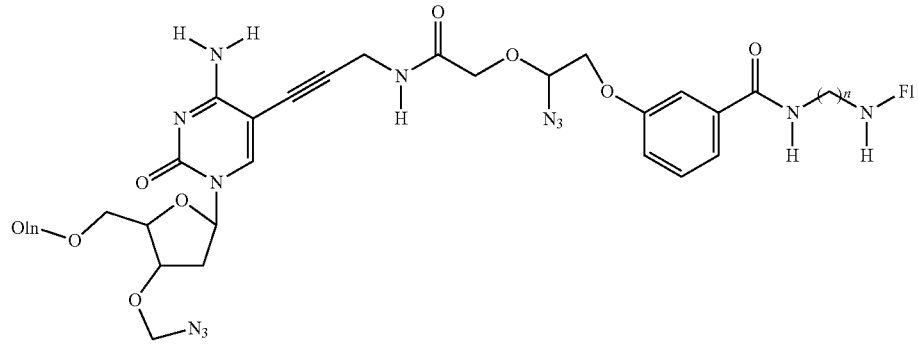
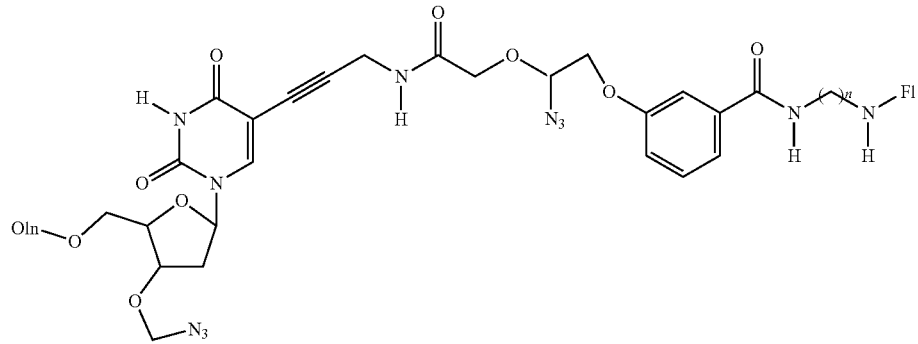

-continued (al)

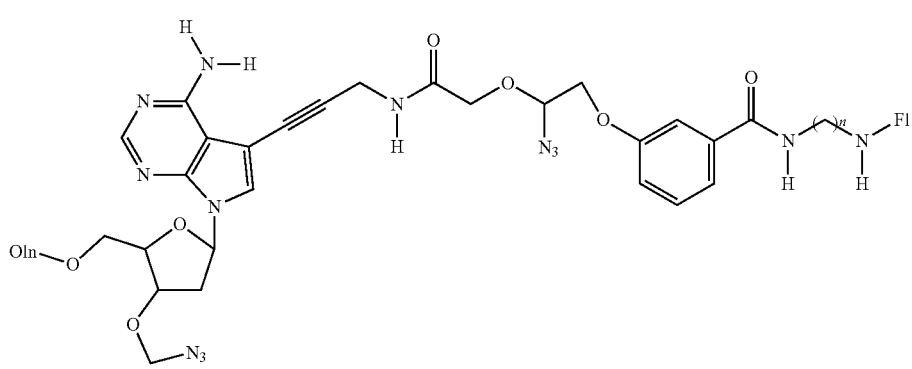

wherein Oln is an oligonucleotide; n is an integer from 2 to 6; and Fl is a fluorophore.

In any of the examples given; n can equal 2 to 6. In any of the examples given; n can equal 2. In any of the examples given; n can equal 3. In any of the examples given; n can equal 4. In any of the examples given; n can equal 5. In any of the examples given; n can equal 6.

Upon detection of the nucleobase incorporated, the fluorescent label and optional linker can be removed. The removal is carried out by reduction of the azido group, leading to fragmentation of the O—CHNH$_2$— moiety. Upon cleavage a hydroxyl group is left attached to the nucleobase and the fluorescent moiety is detached.

Thus disclosed is a compound of the formula (II):

(II)

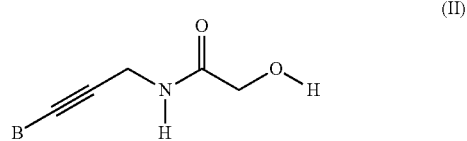

wherein B is a nucleotide base.

The nucleobase can be a purine or a pyrimidine. The common naturally occurring purines are adenine (A) and guanine (G). The common naturally occurring pyrimidines are cytidine (C) and thymine (T) in DNA strands or uracil (U) in RNA strands. The ribose can be a 2'-deoxyribose (in DNA).

The compound of formula II can be attached to an oligonucleotide. Thus moiety B can be a base attached to further bases. Thus disclosed is an oligonucleotide where the 3'-nucleotide is a compound of formula (ci), formula (ti) or formula (ai):

(ci)

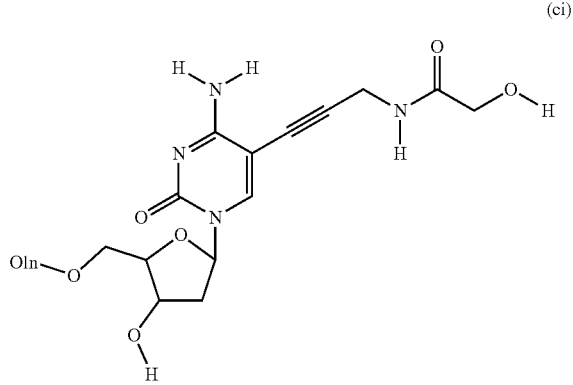

(ti)

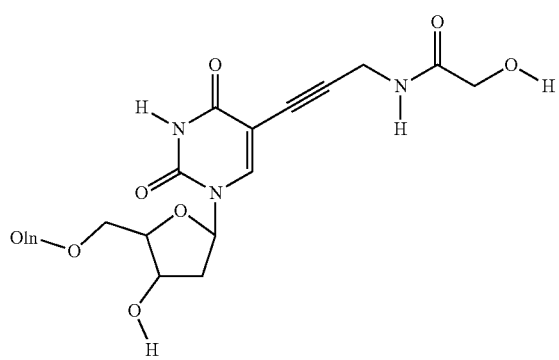

(ai)

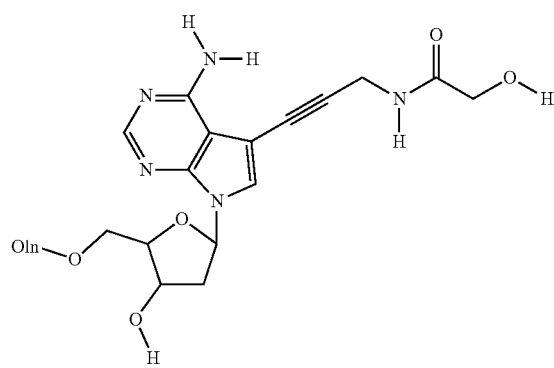

wherein Oln is an oligonucleotide.

The oligonucleotide having the hydroxyl pendant arm can have multiple pendant arms on the same oligonucleotide. The bases modified with the pendant arms would usually be contiguous in a sequence. Disclosed is an oligonucleotide comprising two or more copies of a compound according to formula (II). Disclosed is an oligonucleotide comprising ten or more copies of a compound according to formula (II). Disclosed is an oligonucleotide comprising one hundred or more copies of a compound according to formula (II).

Incorporation of nucleotides can be performed using solutions having more than one type of nucleotide. Thus disclosed is a kit comprising two or more nucleotides wherein at least one nucleotide is a labelled nucleotide as described herein. The kit may comprise two or more nucleotides wherein at least two nucleotides are labelled nucleotides as described herein. The kit may comprise four nucleotides wherein at least two nucleotides are labelled nucleotides as described herein.

The nucleosides, nucleotides, oligonucleotides and kits as described herein can be used in sequencing, expression analysis, hybridization analysis, genetic analysis, RNA analysis or protein binding assays, or combinations thereof.

Provided herein are kits including two or more nucleotides wherein at least one nucleotide is a nucleotide of the present disclosure. The kit may include two or more labelled nucleotides. The nucleotides may be labelled with two or more fluorescent labels. Two or more of the labels may be excited using a single excitation source, which may be a laser. For example, the excitation bands for the two or more labels may be at least partially overlapping such that excitation in the overlap region of the spectrum causes both labels to emit fluorescence. In particular embodiments, the emission from the two or more labels will occur in different regions of the spectrum such that presence of at least one of the labels can be determined by optically distinguishing the emission.

The kit may contain four labelled nucleotides, where the first of four nucleotides is as disclosed herein. In such a kit, the second, third, and fourth nucleotides can each be labelled with a compound that is optionally spectrally different from the label on the first nucleotide and optionally spectrally different from the labels on each other. Thus, one or more of the compounds can have a distinct absorbance maximum and/or emission maximum such that the compound(s) is(are) distinguishable from other compounds. For example, each compound can have a distinct absorbance maximum and/or emission maximum such that each of the compounds is distinguishable from the other three compounds. It will be understood that parts of the absorbance spectrum and/or emission spectrum other than the maxima can differ and these differences can be exploited to distinguish the compounds. The kit may be such that two or more of the compounds have a distinct absorbance maximum above 600 nm. The compounds of the invention typically absorb light in the region above 640 nm.

The compounds, nucleotides or kits that are set forth herein may be used to detect, measure or identify a biological system (including, for example, processes or components thereof). Exemplary techniques that can employ the compounds, nucleotides or kits include sequencing, expression analysis, hybridization analysis, genetic analysis, RNA analysis, cellular assay (e.g. cell binding or cell function analysis), or protein assay (e.g. protein binding assay or protein activity assay). The use may be on an automated instrument for carrying out a particular technique, such as an automated sequencing instrument. The sequencing instrument may contain two lasers operating at different wavelengths.

The present disclosure provides conjugates of fluorescently labelled nucleosides and nucleotides (modified nucleotides). Labelled nucleosides and nucleotides are useful for labelling polynucleotides formed by enzymatic synthesis, such as, by way of non-limiting example, in PCR amplification, isothermal amplification, solid phase amplification, polynucleotide sequencing (e.g. solid phase sequencing), nick translation reactions and the like.

Nucleosides and nucleotides may be labelled at sites on the sugar or nucleobase. As known in the art, a "nucleotide" consists of a nitrogenous base, a sugar, and one or more phosphate groups. In RNA the sugar is ribose and in DNA is a deoxyribose, i.e. a sugar lacking a hydroxyl group that is present in ribose. The nitrogenous base is a derivative of purine or pyrimidine. The purines can be adenine (A) or guanine (G), and the pyrimidines can be cytosine (C), thymine (T) or in the context of RNA, uracil (U). The C-1 atom of deoxyribose is bonded to N-1 of a pyrimidine or N-9 of a purine. A nucleotide is also a phosphate ester of a nucleoside, with esterification occurring on the hydroxyl group attached to the C-3 or C-5 of the sugar. Nucleotides are usually mono-, di- or triphosphates.

A "nucleoside" is structurally similar to a nucleotide but is missing the phosphate moieties. An example of a nucleoside analog would be one in which the label is linked to the base and there is no phosphate group attached to the sugar molecule.

Although the base is usually referred to as a purine or pyrimidine, the skilled person will appreciate that derivatives and analogues are available which do not alter the capability of the nucleotide or nucleoside to undergo Watson-Crick base pairing. "Derivative" or "analogue" means a compound or molecule whose core structure is the same as, or closely resembles that of a parent compound but which has a chemical or physical modification, such as, for example, a different or additional side group, which allows the derivative nucleotide or nucleoside to be linked to another molecule. For example, the base may be a deazapurine. In particular embodiments, the derivatives are capable of undergoing Watson-Crick pairing. "Derivative" and "analogue" also include, for example, a synthetic nucleotide or nucleoside derivative having modified base moieties and/or modified sugar moieties. Such derivatives and analogues are discussed in, for example, Scheit, Nucleotide analogs (John Wiley & Son, 1980) and Uhlman et al., Chemical Reviews 90:543-584, 1990. Nucleotide analogues can also have modified phosphodiester linkages including phosphorothioate, phosphorodithioate, alkyl-phosphonate, phosphoranilidate, phosphoramidate linkages and the like.

The fluorophore may be attached to any position on a nucleotide base, for example, through a linker. In particular embodiments Watson-Crick base pairing can still be carried out for the resulting analogue. Particular nucleobase labelling sites include the C5 position of a pyrimidine base or the C7 position of a 7-deaza purine base. As described above a linker group may be used to covalently attach a dye to the nucleoside or nucleotide. In particular embodiments the labelled nucleoside or nucleotide may be enzymatically incorporable and enzymatically extendable. Accordingly a linker moiety may be of sufficient length to connect the nucleotide to the compound such that the compound does not significantly interfere with the overall binding and recognition of the nucleotide by a nucleic acid replication enzyme. Thus, the linker can also comprise a spacer unit. The spacer distances, for example, the nucleotide base from a cleavage site or label.

Nucleosides or nucleotides labelled according to the disclosure may have the formula:

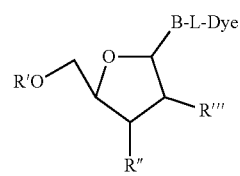

Where Dye is a fluorescent compound, B is a nucleobase, such as, for example uracil, thymine, cytosine, adenine, guanine and the like and L is an optional linker group which may or may not be present. R' can be H, monophosphate, diphosphate, triphosphate, thiophosphate, a phosphate ester analog, —O— attached to a reactive phosphorous containing group or —O— protected by a blocking group. R" can be H, OH, a phosphoramidite or a 3'OH blocking group and R'" is H or OH. Where R" is phosphoramidite, R' is an acid-cleavable hydroxyl protecting group which allows subsequent monomer coupling under automated synthesis conditions.

In another alternative embodiment there is no blocking group on the 3' carbon of the pentose sugar and the dye (or dye and linker construct) attached to the base, for example, can be of a size or structure sufficient to act as a block to the incorporation of a further nucleotide. Thus the block can be due to steric hindrance or can be due to a combination of size, charge and structure, whether or not the dye is attached to the 3' position of the sugar.

In another alternative embodiment the blocking group is present on the 2' or 4' carbon of the pentose sugar and can be of a size or structure sufficient to act as a block to the incorporation of a further nucleotide.

The use of a blocking group allows polymerization to be controlled, such as by stopping extension when a modified nucleotide is incorporated. If the blocking effect is reversible, for example by way of non-limiting example by changing chemical conditions or by removal of a chemical block, extension can be stopped at certain points and then allowed to continue.

In another particular embodiment a 3'OH blocking group will comprise moieties disclosed in WO2004/018497. For example the blocking group may be azidomethyl ($CH_2N_3$) or allyl.

In a particular embodiment a linker (between dye and nucleotide) and a blocking group are both present and are separate moieties. In particular embodiments the linker and blocking group are both cleavable under substantially similar conditions. Thus deprotection and deblocking processes may be more efficient since only a single treatment will be required to remove both the dye compound and the block. However, in some embodiments a linker and blocking group need not be cleavable under similar conditions, instead being individually cleavable under distinct conditions.

This disclosure also encompasses polynucleotides incorporating fluorescent compounds. Such polynucleotides may be DNA or RNA comprised respectively of deoxyribonucleotides or ribonucleotides joined in phosphodiester linkage. Polynucleotides according to the disclosure may comprise naturally occurring nucleotides, non-naturally occurring (or modified) nucleotides other than the modified nucleotides of the disclosure or any combination thereof, in combination with at least one modified nucleotide (e.g. labelled with a dye compound) set forth herein. Polynucleotides according to the disclosure may also include non-natural backbone linkages and/or non-nucleotide chemical modifications. Chimeric structures comprised of mixtures of ribonucleotides and deoxyribonucleotides comprising at least one modified nucleotide according to the disclosure are also contemplated.

Modified nucleotides (or nucleosides) comprising a fluorescent compound according to the present disclosure may be used in any method of analysis such as methods that include detection of a fluorescent label attached to a nucleotide or nucleoside, whether on its own or incorporated into or associated with a larger molecular structure or conjugate. In this context the term "incorporated into a polynucleotide" can mean that the 5' phosphate is joined in phosphodiester linkage to the 3' hydroxyl group of a second (modified or unmodified) nucleotide, which may itself form part of a longer polynucleotide chain. The 3' end of a modified nucleotide set forth herein may or may not be joined in phosphodiester linkage to the 5' phosphate of a further (modified or unmodified) nucleotide. Thus, in one non-limiting embodiment the disclosure provides a method of detecting a modified nucleotide incorporated into a polynucleotide which comprises: (a) incorporating at least one modified nucleotide of the disclosure into a polynucleotide and (b) detecting the modified nucleotide(s) incorporated into the polynucleotide by detecting the fluorescent signal from the dye compound attached to said modified nucleotide(s).

This method can include: a synthetic step (a) in which one or more modified nucleotides according to the disclosure are incorporated into a polynucleotide and a detection step (b) in which one or more modified nucleotide(s) incorporated into the polynucleotide are detected by detecting or quantitatively measuring their fluorescence.

In one embodiment of the present disclosure at least one modified nucleotide is incorporated into a polynucleotide in a synthetic step by the action of a polymerase enzyme. However, other methods of joining modified nucleotides to polynucleotides, such as for example chemical oligonucleotide synthesis or ligation of labelled oligonucleotides to unlabelled oligonucleotides can be used. Therefore, the term "incorporating", when used in reference to a nucleotide and polynucleotide, can encompass polynucleotide synthesis by chemical methods as well as enzymatic methods.

In a specific embodiment a synthetic step is carried out and may optionally comprise incubating a template polynucleotide strand with a reaction mixture comprising fluorescently labelled modified nucleotides of the disclosure. A polymerase can also be provided under conditions which permit formation of a phosphodiester linkage between a free 3' hydroxyl group on a polynucleotide strand annealed to the template polynucleotide strand and a 5' phosphate group on the modified nucleotide. Thus, a synthetic step can include formation of a polynucleotide strand as directed by complementary base-pairing of nucleotides to a template strand.

In all embodiments of the method, the detection step may be carried out whilst the polynucleotide strand into which the modified nucleotides are incorporated is annealed to a template strand, or after a denaturation step in which the two strands are separated. Further steps, for example chemical or enzymatic reaction steps or purification steps, may be included between a synthetic step and a detection step. In particular, the target strand incorporating the modified nucleotide(s) may be isolated or purified and then processed further or used in a subsequent analysis. By way of example, target polynucleotides labelled with modified nucleotide(s) in a synthetic step may be subsequently used as labelled probes or primers. In other embodiments the product of a synthetic step set forth herein may be subject to further reaction steps and, if desired, the product of these subsequent steps can be purified or isolated.

Suitable conditions for a synthetic step will be well known to those familiar with standard molecular biology techniques. In one embodiment a synthetic step may be analogous to a standard primer extension reaction using nucleotide precursors, including modified nucleotides set forth herein, to form an extended target strand complementary to the template strand in the presence of a suitable polymerase enzyme. In other embodiments a synthetic step may itself form part of an amplification reaction producing a labelled double stranded amplification product comprised of annealed complementary strands derived from copying of target and template polynucleotide strands. Other exemplary synthetic steps include nick translation, strand displacement polymerisation, random primed DNA labelling etc. A particularly useful polymerase enzyme for a synthetic step is one that is capable of catalysing the incorporation of one or more of the modified nucleotides set forth herein. A variety of naturally occurring or modified polymerases can be used. By way of example, a thermostable polymerase can be used for a synthetic reaction that is carried out using thermocycling conditions, whereas a thermostable polymerase may not be desired for isothermal primer extension reactions. Suitable thermostable polymerases which are capable of incorporating the modified nucleotides according to the disclosure include those described in WO 2005/024010 or WO06120433. In synthetic reactions which are carried out at lower temperatures such as 37° C., polymerase enzymes need not necessarily be thermostable polymerases, therefore the choice of polymerase will depend on a number of factors such as reaction temperature, pH, strand-displacing activity and the like.

In specific non-limiting embodiments the disclosure encompasses methods of nucleic acid sequencing, re-sequencing, whole genome sequencing, single nucleotide polymorphism scoring, or any other application involving the detection of the modified nucleotide or nucleoside labelled with dyes set forth herein when incorporated into a polynucleotide. Any of a variety of other applications benefitting from the use of polynucleotides labelled with the modified nucleotides comprising fluorophores can use modified nucleotides or nucleosides labelled with dyes set forth herein.

In a particular embodiment the disclosure provides use of modified nucleotides according to the disclosure in a polynucleotide sequencing-by-synthesis reaction. Sequencing-by-synthesis generally involves sequential addition of one or more nucleotides or oligonucleotides to a growing polynucleotide chain in the 5' to 3' direction using a polymerase or ligase in order to form an extended polynucleotide chain complementary to the template nucleic acid to be sequenced. The identity of the base present in one or more of the added nucleotide(s) can be determined in a detection or "imaging" step. The identity of the added base may be determined after each nucleotide incorporation step. The sequence of the template may then be inferred using conventional Watson-Crick base-pairing rules. The use of the modified nucleotides labelled with dyes set forth herein for determination of the identity of a single base may be useful, for example, in the scoring of single nucleotide polymorphisms, and such single base extension reactions are within the scope of this disclosure.

In an embodiment of the present disclosure, the sequence of a template polynucleotide is determined by detecting the incorporation of one or more nucleotides into a nascent strand complementary to the template polynucleotide to be sequenced through the detection of fluorescent label(s) attached to the incorporated nucleotide(s). Sequencing of the template polynucleotide can be primed with a suitable primer (or prepared as a hairpin construct which will contain the primer as part of the hairpin), and the nascent chain is extended in a stepwise manner by addition of nucleotides to the 3' end of the primer in a polymerase-catalyzed reaction.

In particular embodiments each of the different nucleotide triphosphates (A, T, G and C) may be labelled with a unique fluorophore and also comprises a blocking group at the 3' position to prevent uncontrolled polymerization. Alternatively one of the four nucleotides may be unlabelled (dark). The polymerase enzyme incorporates a nucleotide into the nascent chain complementary to the template polynucleotide, and the blocking group prevents further incorporation of nucleotides. Any unincorporated nucleotides can be washed away and the fluorescent signal from each incorporated nucleotide can be "read" optically by suitable means, such as a charge-coupled device using laser excitation and suitable emission filters. The 3'-blocking group and fluorophore compounds can then be removed (deprotected), (simultaneously or sequentially) to expose the nascent chain for further nucleotide incorporation. Typically the identity of the incorporated nucleotide will be determined after each incorporation step but this is not strictly essential. Similarly, U.S. Pat. No. 5,302,509 discloses a method to sequence polynucleotides immobilized on a solid support.

The method, as exemplified above, utilizes the incorporation of fluorescently labelled, 3'-blocked nucleotides A, G, C and T into a growing strand complementary to the immobilized polynucleotide, in the presence of DNA polymerase. The polymerase incorporates a base complementary to the target polynucleotide, but is prevented from further addition by the 3'-blocking group. The label of the incorporated nucleotide can then be determined and the blocking group removed by chemical cleavage to allow further polymerization to occur. The nucleic acid template to be sequenced in a sequencing-by-synthesis reaction may be any polynucleotide that it is desired to sequence. The nucleic acid template for a sequencing reaction will typically comprise a double stranded region having a free 3' hydroxyl group which serves as a primer or initiation point for the addition of further nucleotides in the sequencing reaction. The region of the template to be sequenced will overhang this free 3' hydroxyl group on the complementary strand. The overhanging region of the template to be sequenced may be single stranded but can be double-stranded, provided that a "nick is present" on the strand complementary to the template strand to be sequenced to provide a free 3' OH group for initiation of the sequencing reaction. In such embodiments sequencing may proceed by strand displacement. In certain embodiments a primer bearing the free 3' hydroxyl group may be added as a separate component (e.g. a short oligonucleotide) which hybridizes to a single-stranded region of the template to be sequenced. Alternatively, the primer and the template strand to be sequenced may each form part of a partially self-complementary nucleic acid strand capable of forming an intra-molecular duplex, such as for example a hairpin loop structure. Hairpin polynucleotides and methods by which they may be attached to solid supports are disclosed in International application publication nos. WO0157248 and WO2005/047301. Nucleotides can be added successively to a growing primer, resulting in synthesis of a polynucleotide chain in the 5' to 3' direction. The nature of the base which has been added may be determined, particularly but not necessarily after each nucleotide addition, thus providing sequence information for the nucleic acid template. Thus, a nucleotide is incorporated into a nucleic acid strand (or polynucleotide) by joining of the nucleotide to the free 3' hydroxyl group of the nucleic acid strand via formation of a phosphodiester linkage with the 5' phosphate group of the nucleotide.

The nucleic acid template to be sequenced may be DNA or RNA, or even a hybrid molecule comprised of deoxynucleotides and ribonucleotides. The nucleic acid template may comprise naturally occurring and/or non-naturally occurring nucleotides and natural or non-natural backbone linkages, provided that these do not prevent copying of the template in the sequencing reaction.

In certain embodiments the nucleic acid template to be sequenced may be attached to a solid support via any suitable linkage method known in the art, for example via covalent attachment. In certain embodiments template polynucleotides may be attached directly to a solid support (e.g. a silica-based support). However, in other embodiments of the disclosure the surface of the solid support may be modified in some way so as to allow either direct covalent attachment of template polynucleotides, or to immobilize the template polynucleotides through a hydrogel or polyelectrolyte multilayer, which may itself be non-covalently attached to the solid support.

Arrays in which polynucleotides have been directly attached to silica-based supports are those for example disclosed in WO00006770, wherein polynucleotides are immobilized on a glass support by reaction between a pendant epoxide group on the glass with an internal amino group on the polynucleotide. In addition, polynucleotides can be attached to a solid support by reaction of a sulphur-based nucleophile with the solid support, for example, as described in WO2005/047301. A still further example of solid-supported template polynucleotides is where the template polynucleotides are attached to hydrogel supported upon silica-based or other solid supports, for example, as described in WO00/31148, WO01/01143, WO02/12566, WO03/014392, U.S. Pat. No. 6,465,178 and WO00/53812.

A particular surface to which template polynucleotides may be immobilized is a polyacrylamide hydrogel. Polyacrylamide hydrogels are described in the references cited above and in WO2005/065814.

DNA template molecules can be attached to beads or microparticles. Attachment to beads or microparticles can be useful for sequencing applications. Bead libraries can be prepared where each bead contains different DNA sequences. Exemplary libraries and methods for their creation are described in Nature. 437, 376-380 (2005); Science. 309, 5741, 1728-1732 (2005). Sequencing of arrays of such beads using nucleotides set forth herein is within the scope of the disclosure.

Template(s) that are to be sequenced may form part of an "array" on a solid support, in which case the array may take any convenient form. Thus, the method of the disclosure is applicable to all types of high density arrays, including single-molecule arrays, clustered arrays and bead arrays. Modified nucleotides labelled with dye compounds of the present disclosure may be used for sequencing templates on essentially any type of array, including but not limited to those formed by immobilization of nucleic acid molecules on a solid support.

However, the modified nucleotides of the disclosure are particularly advantageous in the context of sequencing of clustered arrays. In clustered arrays, distinct regions on the array (often referred to as sites, or features) comprise multiple polynucleotide template molecules. Generally, the multiple polynucleotide molecules are not individually resolvable by optical means and are instead detected as an ensemble. Depending on how the array is formed, each site on the array may comprise multiple copies of one individual polynucleotide molecule (e.g. the site is homogenous for a particular single- or double-stranded nucleic acid species) or even multiple copies of a small number of different polynucleotide molecules (e.g. multiple copies of two different nucleic acid species). Clustered arrays of nucleic acid molecules may be produced using techniques generally known in the art. By way of example, WO 98/44151 and WO00/18957, each of which is incorporated herein, describe methods of amplification of nucleic acids wherein both the template and amplification products remain immobilized on a solid support in order to form arrays comprised of clusters or "colonies" of immobilized nucleic acid molecules. The nucleic acid molecules present on the clustered arrays prepared according to these methods are suitable templates for sequencing using the modified nucleotides labelled with dye compounds of the disclosure.

The modified nucleotides of the present disclosure are also useful in sequencing of templates on single molecule arrays. The term "single molecule array" or "SMA" as used herein refers to a population of polynucleotide molecules, distributed (or arrayed) over a solid support, wherein the spacing of any individual polynucleotide from all others of the population is such that it is possible to individually resolve the individual polynucleotide molecules. The target nucleic acid molecules immobilized onto the surface of the solid support can thus be capable of being resolved by optical means in some embodiments. This means that one or more distinct signals, each representing one polynucleotide, will occur within the resolvable area of the particular imaging device used.

Single molecule detection may be achieved wherein the spacing between adjacent polynucleotide molecules on an array is at least 100 nm, more particularly at least 250 nm, still more particularly at least 300 nm, even more particularly at least 350 nm. Thus, each molecule is individually resolvable and detectable as a single molecule fluorescent point, and fluorescence from said single molecule fluorescent point also exhibits single step photobleaching.

The terms "individually resolved" and "individual resolution" are used herein to specify that, when visualized, it is possible to distinguish one molecule on the array from its neighboring molecules. Separation between individual molecules on the array will be determined, in part, by the particular technique used to resolve the individual molecules. The general features of single molecule arrays will be understood by reference to published applications WO00/06770 and WO 01/57248. Although one use of the modified nucleotides of the disclosure is in sequencing-by-synthesis reactions, the utility of the modified nucleotides is not limited to such methods. In fact, the nucleotides may be used advantageously in any sequencing methodology which requires detection of fluorescent labels attached to nucleotides incorporated into a polynucleotide.

In particular, the modified nucleotides of the disclosure may be used in automated fluorescent sequencing protocols, particularly fluorophore-terminator cycle sequencing based on the chain termination sequencing method of Sanger and co-workers. Such methods generally use enzymes and cycle sequencing to incorporate fluorescently labelled dideoxy-nucleotides in a primer extension sequencing reaction. So called Sanger sequencing methods, and related protocols (Sanger-type), utilize randomized chain termination with labelled dideoxynucleotides.

The present disclosure also provides kits including modified nucleosides and/or nucleotides labelled with fluorophores. Such kits will generally include at least one modified nucleotide or nucleoside labelled as set forth herein together with at least one further component. The further component(s) may be one or more of the components identified in a method set forth above or in the Examples section below. Some non-limiting examples of components that can be combined into a kit of the present disclosure are set forth below.

In a particular embodiment, a kit can include at least one modified nucleotide or nucleoside labelled as set forth herein together with modified or unmodified nucleotides or nucleosides. For example, modified nucleotides labelled according to the disclosure may be supplied in combination with unlabelled or native nucleotides, and/or with fluorescently labelled nucleotides or any combination thereof. Accordingly the kits may comprise modified nucleotides labelled with dyes according to the disclosure and modified nucleotides labelled with other, for example, prior art dye compounds. Combinations of nucleotides may be provided as separate individual components (e.g. one nucleotide type per vessel or tube) or as nucleotide mixtures (e.g. two or more nucleotides mixed in the same vessel or tube).

Where kits comprise a plurality, particularly two, more particularly four, modified nucleotides labelled with a dye compound, the different nucleotides may be labelled with different dye compounds, or one may be dark, with no dye compounds. Where the different nucleotides are labelled with different dye compounds it is a feature of the kits that said dye compounds are spectrally distinguishable fluorophores. As used herein, the term "spectrally distinguishable fluorophores" refers to fluorophores that emit fluorescent energy at wavelengths that can be distinguished by fluorescent detection equipment (for example, a commercial capillary based DNA sequencing platform) when two or more such dyes are present in one sample. When two modified nucleotides labelled with fluorophore compounds are supplied in kit form, it is a feature of some embodiments that the spectrally distinguishable fluorophores can be excited at the same wavelength, such as, for example by the same laser. When four modified nucleotides labelled with fluorophore compounds are supplied in kit form, it is a feature of some embodiments that two of the spectrally distinguishable fluorophores can both be excited at one wavelength and the other two spectrally distinguishable dyes can both be excited at another wavelength. Particular excitation wavelengths are 532 nm, 630 nm to 700 nm, particularly 660 nm.

In one embodiment a kit includes a modified nucleotide labelled with a compound of the present disclosure and a second modified nucleotide labelled with a second dye wherein the dyes have a difference in absorbance maximum of at least 10 nm, particularly 20 nm to 50 nm. More particularly the two dye compounds have Stokes shifts of between 15-40 nm where "Stokes shift" is the distance between the peak absorption and peak emission wavelengths.

In a further embodiment a kit can further include two other modified nucleotides labelled with fluorophores wherein the dyes are excited by the same laser at 488 nm to 550 nm, particularly 532 nm. The dyes can have a difference in absorbance maximum of at least 10 nm, particularly 20 nm to 50 nm. More particularly the two dye compounds can have Stokes shifts of between 20-40 nm. Still yet more particularly the two dye compounds can have a different absorbance maximum below 640 nm, particularly below 600 nm. Particular dyes which are spectrally distinguishable from polymethine dyes of the present disclosure and which meet the above criteria are polymethine analogues as described in U.S. Pat. No. 5,268,486 (for example Cy3) or WO 0226891 (Alexa 532; Molecular Probes A20106) or unsymmetrical polymethines as disclosed in U.S. Pat. No. 6,924,372. Alternative dyes include rhodamine analogues, for example tetramethyl rhodamine and analogues thereof.

In an alternative embodiment, the kits of the disclosure may contain nucleotides where the same base is labelled with two different compounds. A first nucleotide may be labelled with a first fluorescent compound, for example a 'red' fluorophore absorbing at greater than 650 nm. A second nucleotide may be labelled with a spectrally distinct compound, for example a 'green' fluorophore absorbing at less than 600 nm. A third nucleotide may be labelled as a mixture of the first fluorophore and the spectrally distinct compound, and the fourth nucleotide may be 'dark' and contain no label. In simple terms therefore the nucleotides 1-4 may be labelled 'green', 'red', 'red/green', and dark. To simplify the instrumentation further, four nucleotides can be labelled with a two dyes excited with a single laser, and thus the labelling of nucleotides 1-4 may be 'red 1', 'red 2' 'red 1/red 2', and dark or 'green 1', 'green 2' 'green 1/green 2', and dark.

Although kits are exemplified above in regard to configurations having different nucleotides that are labelled with different dye compounds, it will be understood that kits can include 2, 3, 4 or more different nucleotides that have the same dye compound.

In particular embodiments a kit may include a polymerase enzyme capable of catalyzing incorporation of the modified nucleotides into a polynucleotide. Other components to be included in such kits may include buffers and the like. The modified nucleotides labelled with dyes according to the disclosure, and other any nucleotide components including mixtures of different nucleotides, may be provided in the kit in a concentrated form to be diluted prior to use. In such embodiments a suitable dilution buffer may also be included. Again, one or more of the components identified in a method set forth herein can be included in a kit of the present disclosure.

It is noted that, as used in this specification and the appended claims, the singular forms "a", "an" and "the" include plural referents unless expressly and unequivocally limited to one referent. It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

EXAMPLES

Additional embodiments are disclosed in further detail in the following examples, which are not in any way intended to limit the scope of the claims.

Example 1

Synthesis of Short-pendant Arm Nucleotide Triphosphate

Scheme 1: Example of synthesis of two short pendant arm nucleotide triphosphate (pppT-sPA-Fl and pppT-sPA2-Fl, where Fl is a fluorophore)

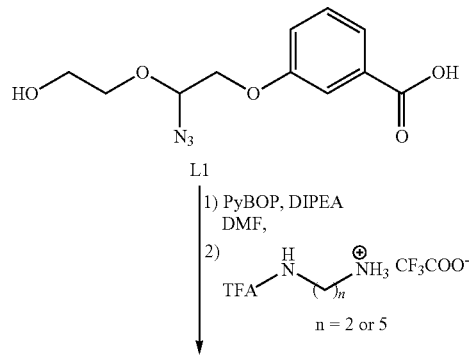

-continued
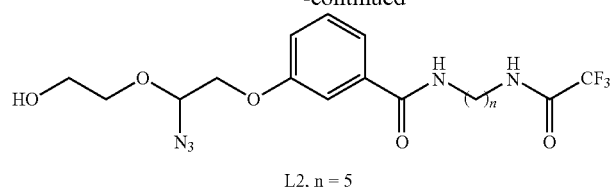
L2, n = 5
L3, n = 2
↓ TEMPO, NaClO, NaClO₂, NaH₂PO₄, H₂O, CH₃CN
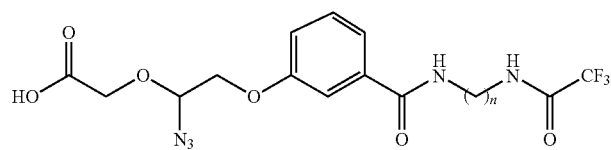
sPA LN3 TFA, n = 5
sPA2 LN3 TFA, n = 2
1) TSTU, DMF. DIPEA
2)
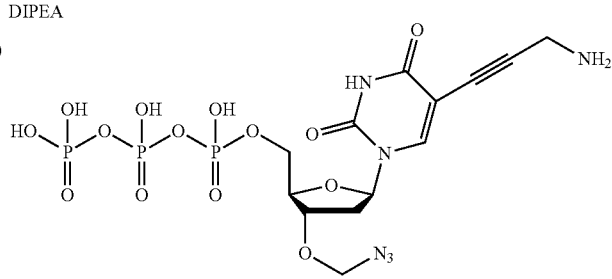
PA-TTP
3) NH₃ aq., MeOH
↓
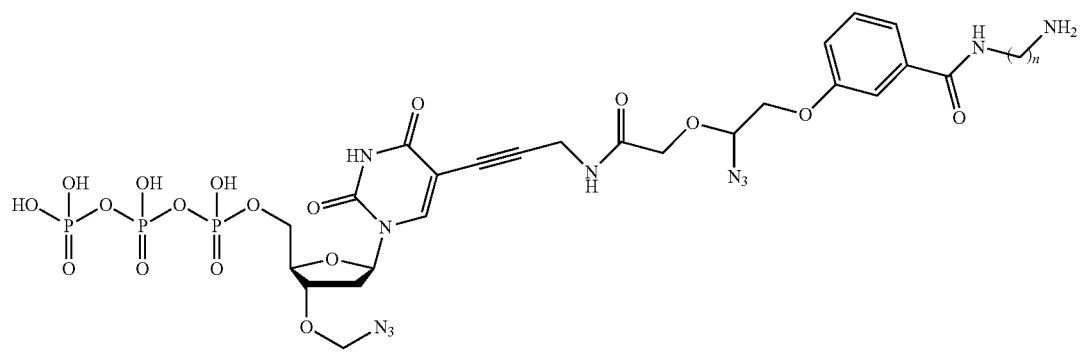
pppT-sPA, n = 5
pppT-sPA2, n = 2
↓ 1) TSTU, DMA. DIPEA, Fl

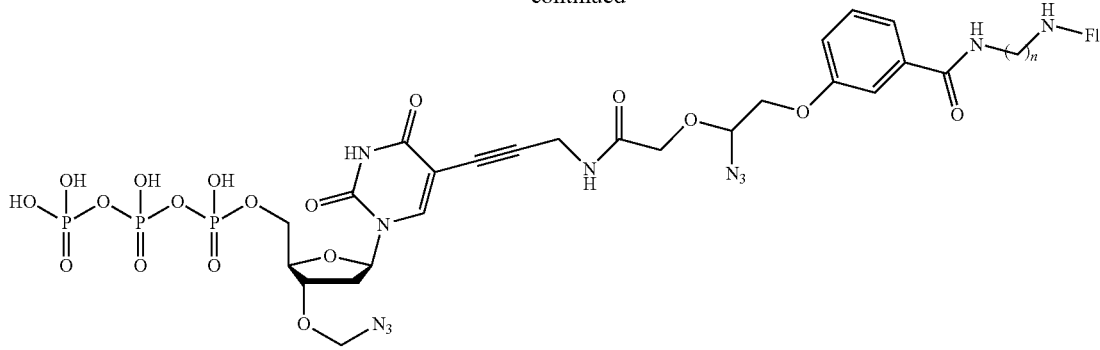

pppT-sPA-Fl, n = 5
pppT-sPA2-Fl, n = 2

Synthesis of Intermediate L2

The starting material L1 (1.07 g, 4 mmol) was dissolved in anhydrous DMF (15 mL), then placed under nitrogen at 0° C. in an ice bath. N,N-diisopropylethylamine (884 µL, 4.8 mmol) was added, followed by PyBOP (2.29 g, 4.4 mmol). The reaction was stirred under nitrogen at 0° C. for 20 minutes. Then N-(5-aminopentyl)-2,2,2-trifluoroacetamide, trifluoroacetate salt (1.5 g, 4.8 mmol) was added, followed by N,N-diisopropylethylamine (1 mL, 5.4 mmol). The reaction was removed from the ice bath and stirred at room temperature for 3 hours. The solvent was removed under reduced pressure and the residue dissolved in ethyl acetate (100 mL). The solution was extracted with 3×100 mL of diluted $KHSO_4$ aq. (pH=1), 1×50 mL of water, 2×100 mL of sat. $NaHCO_3$ aq. The organic phase was dried on $Na_2SO_4$ anhydrous and the solvent was removed under reduced pressure. The crude was purified by flash chromatography on silica gel (linear gradient of ethyl acetate in DCM, from 50% to 100%). L2 was isolated as a clear viscous oil (1.60 g, 3.59 mmol, 90%). $^1$H NMR (400 MHz, $CDCl_3$): δ (ppm) 7.45 (m, 1H, Ar CH), 7.33 (m, 2H, Ar CH), 7.07 (m, 2H, Ar CH, NH), 6.57 (t, J=5.6 Hz, 1H, NH), 4.85 (t, J=4.9 Hz, 1H, CH—$N_3$), 4.22 (dd, J=10.4, 5.1 Hz, 1H, $CH_2$—OAr), 4.16 (dd, J=10.5, 4.7 Hz, 1H, $CH_2$—OAr), 4.00 (ddd, J=10.1, 4.9, 2.9 Hz, 1H, $CH_2$—O), 3.83 (m, 2H, $CH_2$—OH), 3.75 (ddd, J=9.8, 6.6, 3.0 Hz, 1H, $CH_2$—O), 3.45 (q, J=6.7 Hz, 2H, $CH_2$—NH), 3.36 (q, J=6.6 Hz, 2H, $CH_2$—NH), 2.78 (t, J=6.2 Hz, 1H, OH), 1.65 (m, 4H, $CH_2$—$CH_2$—NH), 1.41 (p, J=7.4, 6.9 Hz, 2H, $CH_2$—$CH_2$—$CH_2$—NH). $^{19}$F NMR (376.5 MHz, $CDCl_3$): δ (ppm) –75.7. $^{13}$C NMR (100 MHz, $CDCl_3$): δ (ppm) 167.5 (s), 158.2 (s), 137.5 (s), 135.9 (s), 129.7 (d), 128.2 (d), 119.6 (d), 118.5 (d), 113.2 (d), 89.9 (d), 71.4 (t), 69.4 (t), 61.6 (t), 39.7 (t), 39.4 (t), 29.0 (t), 28.1 (t), 23.6 (t). LC-MS (ES and CI): (–ve) m/z 446 (M–$H^+$); (+ve) m/z 448 (M+$H^+$), 470 (M+$Na^+$).

Synthesis of Linker sPA LN3 TFA

The alcohol L2 (500 mg, 1.12 mmol) was dissolved in acetonitrile (15 mL), then TEMPO (70 mg, 0.448 mmol) was added to it. $NaH_2PO_4$.$2H_2O$ (1.1 g, 7.2 mmol) and $NaClO_2$ (405 mg, 4.48 mmol) were dissolved in 10 mL of water and added to the reaction. Then NaClO aq. (14.5% available chlorine, 1.32 mL, 2.24 mmol) was added and the solution turned immediately dark brown. The reaction was stirred at room temperature for 6 hours. During this time the brown colour faded to orange. The reaction was quenched with conc. $Na_2S_2O_3$ aq. until the reaction turned colourless. Acetonitrile was evaporated under reduced pressure and the solution was diluted with 20 mL of water and basified with triethylamine (approx. 1 mL). The solution was extracted with 10 mL of ethyl acetate and the aqueous phase was concentrated under reduced pressure. The crude sPA LN3 TFA was purified by reverse phase chromatography on C18 (linear gradient of acetonitrile in water from 0% to 30%) and isolated as a clear oil (438 mg, 0.95 mmol, 85%). RP-HPLC: $t_R$=17.9 min (0.1 M TEAB/acetonitrile gradient from 5 to 50%, on YMC-C18 analytical column). $^1$H NMR (400 MHz, $CD_3CN$): δ (ppm) 8.03 (br s, 1H, NH), 7.63 (s, 1H, NH), 7.54 (s, 1H, Ar), 7.42 (d, J=7.7 Hz, 1H, Ar), 7.34 (t, J=7.9 Hz, 1H, Ar), 7.08 (d, J=8.1 Hz, 1H, Ar), 5.10 (m, 1H, CH—$N_3$), 4.35 (dd, J=10.9, 3.7 Hz, 1H, $CH_2$O), 4.18 (dd, J=10.8, 6.1 Hz, 1H, $CH_2$O), 4.09 (m, 2H, $CH_2$O), 3.32 (m, 2H, $CH_2$—NH), 3.27 (m, 2H, $CH_2$—NH), 3.02 (q, J=7.3 Hz, 2H, $Et_3$N), 1.60 (m, 4H, $CH_2$—$CH_2$—NH), 1.39 (m, 2H, $CH_2$—$CH_2$—$CH_2$—NH), 1.21 (t, J=7.3 Hz, 2H, $Et_3$N). $^{19}$F NMR (376.5 MHz, $CD_3CN$): δ (ppm) –76.5. $^{13}$C NMR (100 MHz, $CD_3OD$): δ (ppm) 173.1 (s), 170.0 (s), 159.9 (s), 137.5 (s), 131.0 (d), 125.7 (d), 121.4 (d), 119.2 (d), 114.5 (d), 90.8 (d), 70.5 (t), 66.7 (t), 41.0 (t), 40 µ.8 (t), 30.2 (t), 29.7 (t), 25.4 (t). LC-MS (ES and CI): (–ve) m/z 460 (M–$H^+$). (+ve) m/z 484 (M+$Na^+$), 561 (M+$Et_3NH^+$)

Synthesis of Intermediate L3

The starting material L1 (658 mg, 2.46 mmol) was dissolved in anhydrous DMF (10 mL), then placed under nitrogen at 0° C. in an ice bath. N,N-diisopropylethylamine (544 µL, 2.95 mmol) was added, followed by PyBOP (1.41 g, 2.71 mmol). The reaction was stirred under nitrogen at 0° C. for 20 minutes, then N-(2-aminoethyl)-2,2,2-trifluoroacetamide, trifluoroacetate salt (796 mg, 2.95 mmol) was added, followed by N,N-diisopropylethylamine (589 µL, 3.2 mmol). The reaction was removed from the ice bath and stirred at room temperature for 3 hours. The solvent was removed under reduced pressure and the residue dissolved in ethyl acetate (100 mL). The solution was extracted with 3×100 mL of diluted $KHSO_4$ aq. (pH=1), 1×50 mL of water, 2×100 mL of sat. $NaHCO_3$ aq. The organic phase was dried over $Na_2SO_4$ anhydrous and the solvent was removed under reduced pressure. The crude was purified by flash chromatography on silica gel (linear gradient of ethyl acetate in DCM, from 50% to 100%) and isolated as a viscous oil (0.91 g, 2.24 mmol, 91%). $^1$H NMR (400 MHz, $CDCl_3$): δ (ppm) 8.19 (br s, 1H, NH), 7.39 (d, J=1.7 Hz, 1H, Ar CH), 7.38-7.30 (m, 2H, Ar), 7.24 (t, J=5.5 Hz, 1H, Ar CH), 7.07 (dt, J=7.2, 2.1 Hz, 1H, Ar CH), 4.84 (t, J=4.9 Hz, 1H, CH—$N_3$), 4.20 (dd, J=10.5, 5.1 Hz, 1H, $CH_2$—OAr), 4.15 (dd, J=6.0, 4.5 Hz, 1H, $CH_2$—OAr), 4.00 (ddd, J=10.2, 4.8, 3.0 Hz, 1H, $CH_2$—O), 3.88-3.79 (m, 2H, $CH_2$—OH), 3.74 (ddd, J=9.8, 6.4, 3.2 Hz, 1H, $CH_2$—O), 3.65 (m, 2H, $CH_2$—NH), 3.58 (m, 2H, $CH_2$—NH), 2.82 (t, J=5.6 Hz 1H, OH). $^{19}$F NMR (376.5 MHz, CDCl$_3$): δ (ppm) −75.9. LC-MS (ES and CI): (−ve) m/z 404 (M−H$^+$); (+ve) m/z 406 (M+H$^+$), 428 (M+Na$^+$)

Synthesis of sPA2 LN3 TFA

The alcohol L3 (230 mg, 0.567 mmol) was dissolved in acetonitrile (10 mL), then TEMPO (35 mg, 0.27 mmol) was added to it. NaH$_2$PO$_4$.2H$_2$O (575 mg, 3.68 mmol) and NaClO$_2$ (205 mg, 2.26 mmol) were dissolved in 10 mL of water and added to the reaction. Then NaClO aq. (14.5% chlorine content, 0.671 mL, 1.13 mmol) was added and the solution turned immediately dark brown. The reaction was stirred at room temperature for 18 hours. During this time the brown colour faded to orange. The reaction was quenched with conc. Na$_2$S$_2$O$_3$ aq. until it turned colourless. Acetonitrile was evaporated under reduced pressure and the solution was diluted with 10 mL of water, basified with triethylamine (approx. 0.6 mL) and extracted with 10 mL of ethyl acetate. The aqueous phase was concentrated under reduced pressure. The crude sPA2 LN3 TFA was purified by reverse phase chromatography on C18 (linear gradient of acetonitrile in water from 0% to 20%) and isolated as clear oil (224 mg as triethylammonium salt, 0.43 mmol, 77%). RP-HPLC: $t_R$=17.9 min (0.1 M TEAB/acetonitrile gradient from 5% to 40%, on YMC-C18 analytical column). $^1$H NMR (400 MHz, CD$_3$CN): δ (ppm) 8.52 (br s, 1H, NH), 8.34 (br s, 1H, NH), 7.77 (s, 1H, Ar), 7.49 (dt, J=7.7, 1.1 Hz, 1H, Ar), 7.38 (t, J=7.9 Hz, 1H, Ar), 7.10 (ddd, J=8.2, 2.6, 1.0 Hz, 1H, Ar), 5.14 (dd, J=6.7, 3.4 Hz, 1H, CH—N$_3$), 4.48 (dd, J=11.5, 3.4 Hz, 1H, CH$_2$O), 4.20 (dd, J=11.5, 6.7 Hz, 1H, CH$_2$O), 4.11 (d, J=1.4 Hz, 2H, CH$_2$O), 3.66-3.42 (m, 4H, CH$_2$—NH), 3.05 (q, J=7.3 Hz, 5H, Et$_3$N), 1.22 (t, J=7.3 Hz, 8H, Et$_3$N). $^{19}$F NMR (376.5 MHz, CD$_3$CN): δ (ppm) −76.3. $^{13}$C NMR (101 MHz, CD$_3$CN): δ (ppm) 173.1 (s), 166.9 (s), 157.6 (s), 135.7 (s), 129.3 (d), 120.0 (d), 118.0 (d), 117.0 (s), 112.1 (d), 88.4 (d), 68.8 (t), 67.6 (t), 45.1 (t), 39.2 (t), 38.4 (t), 7.5 (q). LC-MS (ES and CI): (−ve) m/z 418 (M−H$^{30}$).

General Synthesis of pppT-sPA and pppT-sPA2

The linker (sPA-LN3-TFA or sPA2-LN3-TFA, 0.089 mmol) was coevaporated with 2×2 mL of anhydrous N,N'-dimethylformamide (DMF), then dissolved in 2 mL of anhydrous DMF. N,N-diisopropylethylamine (33 μL, 0.178 mmol) was added, followed by N,N,N',N'-tetramethyl-O-(N-succinimidyl)uronium tetrafluoroborate (TSTU, 32 mg, 0.106 mmol). The reaction was stirred under nitrogen at room temperature for 1 hour. In the meantime, an aqueous solution of the triphosphate PA-TTP (0.1 mmol) was evaporated to dryness under reduced pressure and resuspended in 300 μL of 0.1 M triethylammonium bicarbonate (TEAB) solution in water. The linker solution was added to the triphosphate and the reaction was stirred at room temperature for 18 hours. Then, the solvent was evaporated under reduced pressure and the residue dissolved in 1 mL of methanol and 3 mL of aqueous ammonium hydroxide 33%. The solution was stirred at room temperature for 7 hours, then evaporated to dryness. The crude was purified by preparative scale RP-HPLC using a YMC-Pack-Pro C18 column eluting with 0.1 M TEAB and acetonitrile. pppT-sPA: Yield: 67%. RP-HPLC: $t_R$=16.9 min (0.1 M TEAB/acetonitrile gradient from 5% to 35%, on YMC-C18 analytical column). LC-MS (ES and CI): (−ve) m/z 922 (M−H$^+$), 461 (M−2H$^+$). pppT-sPA2: Yield: 65%. RP-HPLC: $t_R$=17.5 min (0.1 M TEAB/acetonitrile gradient from 5% to 30%, on YMC-C18 analytical column). LC-MS (ES and CI): (−ve) m/z 880 (M−H$^+$), 440 (M−2H$^+$).

General Synthesis of pppT-sPA-Fl and pppT-sPA2-Fl

A fluorophore carboxylate (Fl, 0.0105 mmol) was coevaporated with 2×2 mL of anhydrous N,N'-dimethylformamide (DMF), then dissolved in 2 mL of anhydrous N,N'-dimethylacetamide DMA. N,N-diisopropylethylamine (15 μL, 0.084 mmol) was added, followed by N,N,N',N'-tetramethyl-O-(N-succinimidyl)uronium tetrafluoroborate (TSTU, 0.012 mmol). The reaction was stirred under nitrogen at room temperature for 45 minutes. In the meantime, an aqueous solution of the triphosphate pppT-sPA or pppT-sPA2 (0.084 mmol) was evaporated to dryness under reduced pressure and resuspended in 300 μL, of 0.1 M triethylammonium bicarbonate (TEAB) solution in water. The fluorophore-NHS ester solution was added to the triphosphate and the reaction was stirred at room temperature for 18 hours. The crude was purified by ion-exchange chromatography on DEAE-Sephadex (gradient from 0.1 M TEAB to 1 M TEAB, with 20% acetonitrile) and by preparative scale RP-HPLC (YMC-Pack-Pro C18 column, eluting with 0.1 M TEAB and acetonitrile).

General Synthesis of N-(aminoalkyl)-2,2,2-trifluoroacetamide

Scheme 2: General synthesis of N-trifluoroacetamido-diamine.

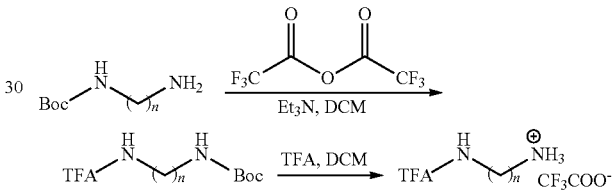

Tert-butyl (aminoalkyl)carbamate (48 mmol) was dissolved in anhydrous DCM (60 mL) and placed in an ice bath under nitrogen. Triethylamine (103 mmol) was added, followed by trifluoroacetic anhydride (53 mmol) dropwise. The reaction was removed from the ice bath and stirred at room temperature for 1 hour. The reaction was diluted with 200 mL of DCM and extracted with 2×200 mL of sat. aq. NaHCO$_3$. The organic phase was dried over MgSO$_4$ anhydrous and concentrated under reduced pressure. The crude was purified by flash chromatography on silica gel (petroleum ether/ethyl acetate 3:7).

tert-butyl (5-(2,2,2-trifluoroacetamido)pentyl)carbamate (n=5): $^1$H NMR (400 MHz, CDCl$_3$): δ (ppm) 6.40 (br s, 1H, NH), 4.49 (br s, 1H, NH), 3.30 (q, J=6.8 Hz, 2H, CH$_2$—NH), 3.06 (q, J=6.6 Hz, 2H, CH$_2$—NH), 1.56 (p, J=7.2 Hz, 2H, CH$_2$.CH$_2$—NH), 1.45 (p, J=7.0 Hz, 2H, CH$_2$.CH$_2$—NH), 1.37 (m, 9H, CH$_3$), 1.31 (m, 2H, CH$_2$.CH$_2$—CH$_2$—NH).$^{19}$F NMR (376.5 MHz, CDCl$_3$): δ (ppm) −75.8.

tert-butyl (2-(2,2,2-trifluoroacetamido)ethyl)carbamate (n=2): $^1$H NMR (400 MHz, CDCl$_3$): δ (ppm) 7.72 (br s, 1H, NH), 4.86 (br s, 1H, NH), 3.39 (m, 2H, CH$_2$—NH), 3.31 (m, 2H, CH$_2$—NH), 1.38 (s, 9H, CH$_3$). $^{19}$F NMR (376.5 MHz, CDCl$_3$): δ (ppm) −76.1.

tert-butyl (2-(2,2,2-trifluoroacetamido)alkyl)carbamate (44 mmol) was dissolved in anhydrous DCM (40 mL) and trifluoroacetic acid (40 mL). The reaction was stirred at room temperature, open to air for 1 hour. The volatiles were removed under reduced pressure. The residue was dissolved in water and extracted with 50 mL of DCM, then the aqueous phase was evaporated to dryness. The residue was coevaporated with 100 mL of ethanol and 4×100 mL of acetonitrile.

N-(5-aminopentyl)-2,2,2-trifluoroacetamide (n=5): $^1$H NMR (400 MHz, d$_6$-DMSO): δ, (ppm) 9.44 (br s, 1H, NH), 7.75 (br s, 3H, NH), 3.17 (q, J=6.7 Hz, 2H, CH$_2$—NH), 2.77 (m, 2H, CH$_2$—NH), 1.57-1.45 (m, 4H, CH$_2$.CH$_2$—NH), 1.29 (m, 2H, CH$_2$—CH$_2$—CH$_2$—NH). $^{19}$F NMR (376.5 MHz, d$_6$-DMSO): δ (ppm) −74.4,-74.7.

N-(2-aminoethyl)-2,2,2-trifluoroacetamide (n=2): $^1$H NMR (400 MHz, d$_6$-DMSO): δ (ppm) 9.58 (br t, 1H, NHCO), 8.04 (br s, 3H, NH), 3.45 (m, 2H, CH$_2$NHCO), 2.98 (m, 2H, CH$_2$NH). $^{19}$F NMR (376.5 MHz, d$_6$-DMSO): δ (ppm) −74.0,-74.4.

Example 2

Use of Short-pendant Arm Nucleotide Triphosphates in SBS Sequencing

Figure 3:
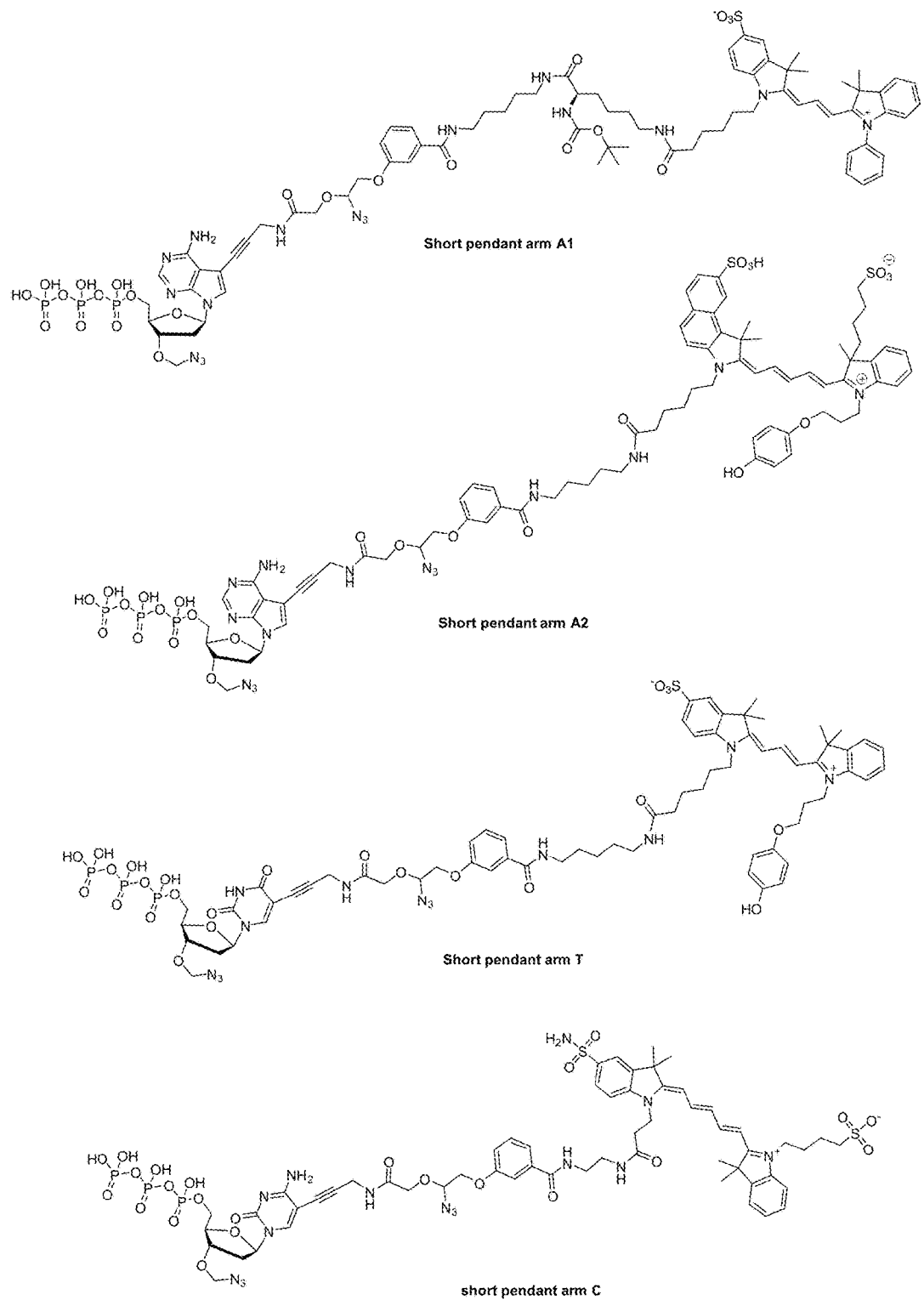
FIG. 3 illustrates examples of four short pendant arm nucleotides for 2-channel SBS sequencing.

The sequencing performance of the short pendant arm nucleotides was compared against that of standard SBS nucleotides, which contained the same fluorescent groups on a standard cleavable linker. Four short pendant arm nucleotides (two As, C, T) labelled with fluorophores suitable for 2-channel SBS sequencing (FIG. 3), and dark G were included in a solution comprising a DNA polymerase and incorporation buffer and used in either a 2-channel modified Hiseq® or 2-channel modified Miseq® to sequence on two reads of 150 cycles each. The sequencing metrics (e.g. phasing, prephasing, percentage error rate and percentage Q30) were compared between experiments carried out using either all four short pendant arms nucleotides or all standard nucleotides, under the same conditions (e.g. incorporation temperature, incorporation time, polymerase, template library). The results are shown in FIGS. 4A-4C and FIGS. 5A and 5B.

FIGS. 4A-4C demonstrate an example of the sequencing metrics (phasing, prephasing, % error rate, % Q30) observed with the standard and the short-pendant arm nucleotides on a 2-channel modified Hiseq®, using 50° C. incorporation temperature and 10 seconds incorporation time, and with two different polymerases (PolA and PolB) and two different template libraries (PhiX and human). When the short pendant arm nucleotides were used, a reduction in phasing and % error rate and an increase of % Q30 was observed, independently on the polymerase or template used.

FIGS. 5A and 5B demonstrate an example of the sequencing metrics (phasing and % error rate) observed with either the standard or the short-pendant arm nucleotides on a 2-channel modified Miseq® at 60° C. incorporation temperature, on a PhiX template, allowing for different incorporation times.

The short pendant arm nucleotides allowed for an approximate 50% reduction of the incorporation time without a significant impact on the percentage error rate. At the shortest incorporation time tested (10+5s), the percentage error rate was still <1%, compared to 2.5% error rate with the standard nucleotides.

What is claimed is:

1. A compound of the formula (I):

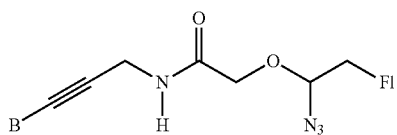

(I)

wherein B is a nucleoside base; and
Fl is a fluorophore attached through an optional linker.

2. The compound according to claim 1, wherein B is a nucleotide base.

3. The compound according to claim 2, wherein B is a pyrimidine base.

4. The compound according to claim 3, wherein the compound is of formula (c) or formula (t):

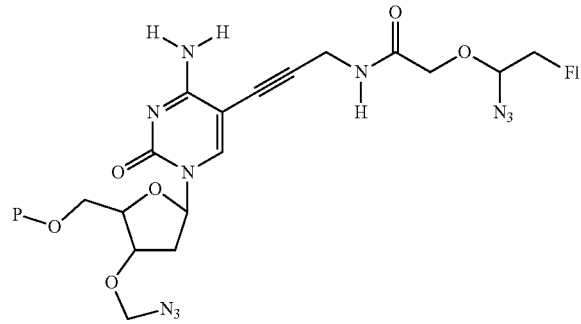

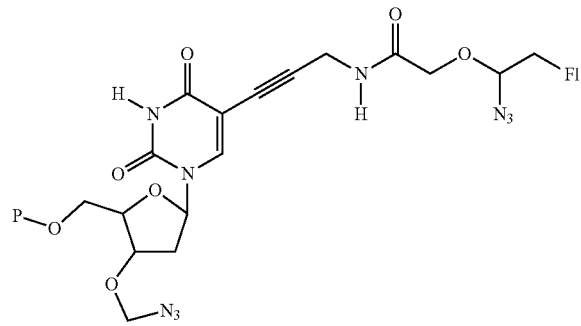

wherein p is a triphosphate group; and
Fl is a fluorophore attached through an optional linker.

5. The compound according to claim 2, wherein B is a 7-deazapurine base.

6. The compound according to claim 5, wherein the compound is of formula (a):

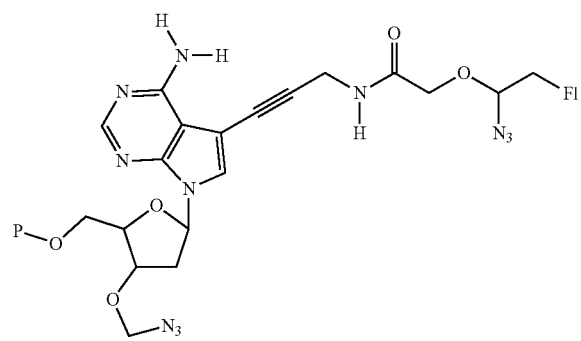

wherein p is a triphosphate group; and
Fl is a fluorophore attached through an optional linker.

7. The compound according to claim 2, wherein the compound is attached to an oligonucleotide.

8. An oligonucleotide labelled with a compound according to claim 2.

9. A compound of the formula (II):

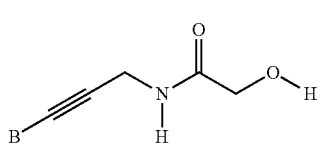

wherein B is a nucleotide base.

10. The compound according to claim 9, wherein B is a pyrimidine base.

11. The compound according to claim 10, wherein the compound is of formula (ci) or formula (ti):

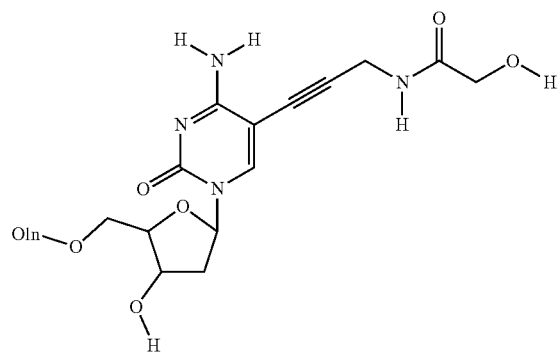

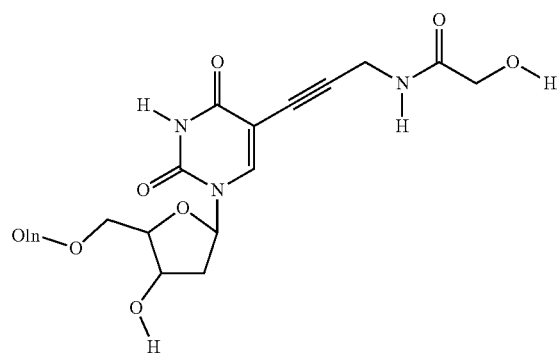

wherein Oln is an oligonucleotide.

12. The compound according to claim 9, wherein B is a 7-deazapurine base.

13. The compound according to claim 12, wherein the compound is of formula (ai):

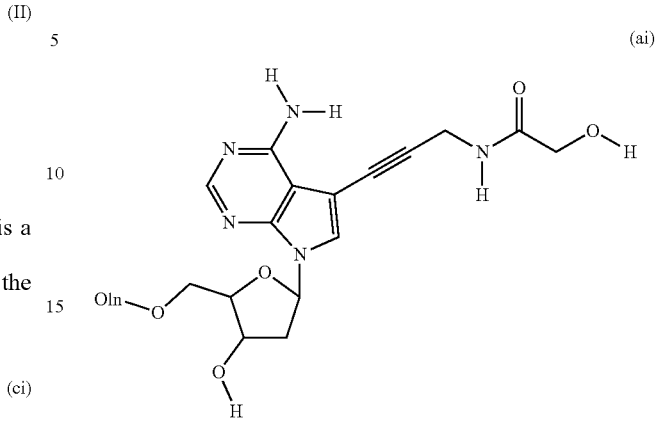

wherein Oln is an oligonucleotide.

14. An oligonucleotide comprising a compound according to claim 9.

15. An oligonucleotide comprising two or more copies of a compound according to claim 9.

16. An oligonucleotide comprising ten or more copies of a compound according to claim 9.

17. An oligonucleotide comprising one hundred or more copies of a compound according to claim 9.

18. A kit comprising two or more nucleotides wherein at least one nucleotide is a labelled nucleotide according to claim 2.

19. The kit according to claim 18, comprising two or more nucleotides wherein at least two nucleotides are labelled nucleotides according to claim 2.

20. The kit according to claim 18, comprising four nucleotides wherein at least two nucleotides are labelled nucleotides according to claim 2.

21. The nucleotide according to claim 2, for use in sequencing, expression analysis, hybridization analysis, genetic analysis, RNA analysis, or protein binding assays, or combinations thereof.

22. The oligonucleotide according to claim 8, for use in sequencing, expression analysis, hybridization analysis, genetic analysis, RNA analysis, or protein binding assays, or combinations thereof.

23. The oligonucleotide according to claim 14, for use in sequencing, expression analysis, hybridization analysis, genetic analysis, RNA analysis, or protein binding assays, or combinations thereof.

* * * * *

UNITED STATES PATENT AND TRADEMARK OFFICE
CERTIFICATE OF CORRECTION

Page 1 of 2

PATENT NO. : 10,526,648 B2
APPLICATION NO. : 16/033118
DATED : January 7, 2020
INVENTOR(S) : Elena Cressina It is certified that error appears in the above-identified patent and that said Letters Patent is hereby corrected as shown below:

In the Specification

In Column 16, Line 38, delete "7-deaza purine" and insert --7-deazapurine--.

In Column 16, Line 62, delete "Where" and insert --where--.

In Column 28, Line 39, after "$NH^+$)" insert --.--.

In Column 29, Line 3, after "$Na^+$)" insert --.--.

In Column 29, Line 39, delete "$H^{30}$" and insert --$H^+$--.

In Column 29, Line 46, delete "uranium" and insert --uronium--.

In Column 30, Line 12, delete "μL," and insert --μL--.

In Column 30, Line 47, delete "tert" and insert --Tert--.

In Column 30, Line 54, delete "tert" and insert --Tert--.

In Column 30, Line 59, delete "tert" and insert --Tert--.

In Column 31, Line 2, delete "$\delta$," and insert --$\delta$--.

In the Claims

In Column 34, Line 31, Claim 18, delete "labelled nucleotide" and insert --labelled compound--.

Signed and Sealed this
Fifth Day of May, 2020

Andrei Iancu
*Director of the United States Patent and Trademark Office*

CERTIFICATE OF CORRECTION (continued)
U.S. Pat. No. 10,526,648 B2

In Column 34, Lines 34-35, Claim 19, delete "labelled nucleotides" and insert --labelled compounds--.

In Column 34, Lines 37-38, Claim 20, delete "labelled nucleotides" and insert --labelled compounds--.

In Column 34, Line 39, Claim 21, delete "nucleotide" and insert --compound--.